United States Patent [19]
Lanza et al.

[11] Patent Number: 6,083,688
[45] Date of Patent: Jul. 4, 2000

[54] PLATELET GLYCOPROTEIN V GENE AND USES

[75] Inventors: Francois Lanza, Schiltigheim, France; David R. Phillips, Oakland, Calif.; Jean-Pierre Cazenave, Lampertheim, France

[73] Assignee: Cor Therapeutics, Inc, South San Francisco, Calif.

[21] Appl. No.: 08/195,006

[22] Filed: Feb. 10, 1994

Related U.S. Application Data

[63] Continuation-in-part of application No. 08/089,455, Jul. 9, 1993, abandoned.
[51] Int. Cl.$^7$ .................................................. C12N 15/12
[52] U.S. Cl. ........................... 435/6; 536/23.5; 536/24.1; 536/24.31; 435/252.3; 435/325
[58] Field of Search .................. 536/23.5, 24.1, 536/24.31; 436/501; 435/69.1, 252.3, 320.1, 172.3, 6, 325

[56] References Cited

PUBLICATIONS

Sambrook et al. Molecular Cloning. Cold Spring Harbor Press, pp. 8.4 and 8.76, 1989.
Modderman et al. (1992) "Glycoproteins V and Ib–IX Form a Noncovalent Complex in the Platelet Membrane", *The Journal of Biological Chemistry,* 267:pp. 364–369.
Berndt et al. (1981) "Purification and Preliminary Physicochemical Characterization of Human Platelet Membrane Glycoprotein V", *The Journal of Biological Chemistry,* 256(1):59–65.
Phillips et al. (1977) "Platelet Plasma Membrane Glycoproteins", *Biochemical and Biophysical Research Communications,* 75(4):940–947.
Sabatini et al. (1982) "Mechanisms for the Incorporation of Proteins in Membranes and Organelles", *The Journal of Cell Biology,* 92:1–22.
Bienz et al. (1986) "Glycoprotein V is not the Thrombin Activation Receptor on Human Blood Platelets", *Blood,* 68(3):720–725.
Zafar et al. (1989) "Platelet Membrane Glycoprotein V: Characterization of the Thrombin–Sensitive Glycoprotein from Human Platelets", *Thrombosis Research* 53:31–44.
Wicki et al. (1989) "Isolation and Characterization of Human Blood Platelet mRNA and Construction of a cDNA Library in λgt11", *Thromb. Haemostas.,* 61(5):448–453.
Shimomura et al. (1990) "Rapid Purification and Characterization of Human Platelet Glycoprotein V: The Amino Acid Sequence Contains Leucine–Rich Repetitive Modules as in Glycoprotein Ib", *Blood,* 75(12):2349–2356.
Roth (1991) "Developing Relationships: Arterial Platelet Adhesion, Glycoprotein Ib, and Leucine–Rich Glycoproteins", *Blood,* 77(1):5–19.
Stubbs et al. (1993) "A Player of Many Parts: The Spotlight Falls on Thrombin's Structure", *Thrombosis Research* 69:1–58.

George et al. (1984) "Molecular Defects in Interactions of Platelets with the Vessel Wall", *The New England Journal of Medicine* 311(17):1084–1098.
Frohman et al. (1988) "Rapid Production of Full–Length cDNAs from Rare Transcripts: Amplification Using a Single Gene–Specific Oligonucleotide Primer", *Proc. Natl. Acad. Sci. USA* 85:8998–9002.
Berndt et al. (1983) "Additional Glycoprotein Defects in Bernard–Soulier's Syndrome: Confirmation of Genetic Basis by Parental Analysis", *Blood* 62(4):800–807.
Lanza et al. (1992) "A New Variant of Glanzmann's Thrombasthenia (Strasbourg I) Platelets with Functionally Defective Glycoprotein IIb–IIIa Complexes and a Glycoprotein IIIa $^{214}$Arg → $^{214}$Trp Mutation", *J. Clin. Invest.,* 89:1995–2004.
Faisst et al. (1992) "Compilation of Vertebrate–encoded Transcription Factors", *Nucleic Acids Research* 20(1):3–26.
Roth et al. (1990) "Human Platelet Glycoprotein V: A Surface Leucine–Rich Glycoprotein Related to Adhesion", *Biochemical and Biophysical Research Communications* 170(1):153–161.
Vu et al. (1991) "Molecular Cloning of a Functional Thrombin Receptor Reveals a Novel Proteolytic Mechanism of Receptor Activation", *Cell* 64:1057–1068.
De Marco et al. (1991) "Function of Glycoprotein Ibα in Platelet Activation Induced by α–Thrombin",*J. Biol. Chem.* 266:23776–23783.
Clemetson et al. (1982) "Characterization of the Platelet Membrane Glycoprotein Abnormalities in Bernard–Soulier Syndrome and Comparison with Normal by Surface–labeling Techniques and High–resolution Two–dimensional Gel Electrophoresis," *J. Clin. Invest.,* 70:304–311.
Nurden et al. (1981) "Analysis of the Glycoprotein and Protein Composition of Bernard–Soulier Platelets by Single and Two–dimensional Sodium Dodecyl Sulfate–Polyacrylamide Gel Electrophoresis," *J. Clin. Invest.,* 67:1431–1440.
Vicente et al. (1990) "Identification of a Site in the α Chain of Platelet Glycoprotein Ib That Participates in von Willebrand Factor Binding," *J. Biol. Chem.,* 265:274–280.
Lopez et al. (1987) "Cloning of the α chain of human platelet glycoprotein Ib: A transmembrane protein with homology to leucine–rich $α_2$–glycoprotein," *Proc. Natl. Acad. Sci. USA,* 84:5615–5619.
Wenger et al. (1988) "Structure of the Human Blood Platelet Membrane Glycoprotein Ibα Gene," *Biochem. Biophys. Res. Commun.,* 156(1):389–395.

(List continued on next page.)

*Primary Examiner*—Lorraine M. Spector
*Assistant Examiner*—Karen E. Brown
*Attorney, Agent, or Firm*—Morgan, Lewis & Bockius LLP

[57] ABSTRACT

This invention relates to the glycoprotein v gene. Specifically, this invention discloses the sequence and structure of the glycoprotein v gene and the amino acid sequence of the glycoprotein v polypeptide. In addition, the evolutionary relationship of the glycoprotein v gene with other glycoproteins is described and several uses of the isolated glycoprotein v gene are shown.

12 Claims, 10 Drawing Sheets

OTHER PUBLICATIONS

Lopez et al. (1988) "The α and β chains of human platelet glycoprotein Ib are both transmembrane proteins containing a leucine–rich amino acid sequence," *Proc. Natl. Acad. Sci. USA*, 85:2135–2139.

Hickey et al. (1993), "Characterization of the Gene Encoding Human Platelet Glycoprotein IX," *J. Biol. Chem.*, 268(5):3438–3443.

Hickey et al. (1989), "Human platelet glycoprotein IX: An adhesive prototype of leucine–rich glycoproteins with flank–center–flank structures," *Proc. Natl. Acad. Sci. USA*, 86:6733–6777.

Hickey et al. (1993), "Human platelet glycoprotein V: Characterization of the polypeptide and the related Ib–V–IX receptor system of adhesive, leucine–rich glycoproteins," *Proc. Natl. Acad. Sci. USA*, 90:8327–8331.

Lanza et al. (1993), "Cloning and Characterization of the Gene Encoding the Human Platelet Glycoprotein V," *J. Biol. Chem.*, 268(28):20801–20807.

```
                   5'-TGATCGGAAC TGAAAGACCT CCCGCGATAC CTGGCAGAGG CAGTGGCTCT    50
                              TRE
TCCCTGTGGT CCAGGGCTGA CTGACTTTGA AGGTAATTTC AGTCAACCCA GCCTTTACTG   110
GGCTCTGACT GCATTAGGCT GCATCAAAGG GGATTGGATC CCATGATTCT TTATATCTTC   170
TGACATTAAG CCTTTGTCAG CTATAGGTGT TACAAATATC TTTAGTTTGT GGTTTATCTT   230
TTCCCCTTTT TTATGGTGTC TTGAAGGATA GAAGTCTTAA TGCAGACAGC ATTATCAGTG   290
TGTTCAAAAG ACAGCTAGAC ACGTTTTGCC TATAGACAAA TGGGCAAAAG GAAACCCAGC   350
TTTCTCAAAT GAAGCACAAG TGGGCCTTAA TTATGTGAAA AGGTGTTCAA GTTCATCATT   410
AAACAGGGAA AGGAAAAGTT AAAACCATGC TGAGATATCT TTCATAGAAA TGGCAAAAAG   470
  Ets-1                               Ets-1
CAGGAAGTGC CACGTGTGGG CAGAGAGGAA GCACAGGAAC TCTCACAAAT GGCAGGTGTC   530
ATCGTAGACC AACACAACCA CTTTGGAGAG CAGTTTGACT TTCCGCAGTT AAACTGAACA   590
TGTGAGCGGC CGGGCGTGGT GGCTCATGCC TGTAATCCCA GCAGTTTGGG AGGCCGAGGC   650
GGGCGGATTG CCTGAGCTCA GGAGTTCAAG ACCAGCCAGG GCAACACGGT AAAACCCCGT   710
CTCTACTAAA ATACAAAAAA TTAGCTGGGC GTGATGGTGT GTGCCTGTAA TCCCAGCTAC   770
TTGTGAGGCC GAGGCAGGAG AATTGCTTGA ACCAGGGAGC AGGAGGTTGC AGTGAGCCGA   830
GATCGCACCA CTGCACCCCA GCCTGGCGAC AGAGTCCCCC TCCCCCACCA AAAAACAAC   890
       Ets-1
AAGTGAGCAT CCTGCAACCT AGCAATGCCA TTGTTGAACA AGTTCAAAGA TGTTCTTAGC   950
CTTATTAGTC CCAAAAGGAA GAAAAAAATG GAGGATTTGA GAATGTTCTT AGCTTTATTG   1010
CTAAGCGGAG AAAGAAAAAC AACACATACC AAAAAAAAAA AAAAAAAAAA AAAAAAACAA   1070
AAAACCTGGG TGGGAAATTA GGGCCATGTG GCATGAAAAG GAAGACCCAG GGGAAGTGTG   1130
            Sp1                                           Ets-1
GCCCATCTAG GGGTGTGGCT ACTGCAGTGA TCCAGCTGTA TCACTGAACT TCCCTGGCAT   1190
         TATA
CATAGAGTTA TATTGTGCCA TTTATGGAAA AACTCTCCCC ACTGCTCTTG GCTTTGACAG   1250
           TATA                    GATA
TAGGAATCAG GTTATATATG GTCTCTCGGT TTGAAGATAT TTGTCATTAA AAACCAGAAC   1310
           GATA                                        Ets-1
AAGGGCTCTG AGATAGGGTC CTTTCCTGAC CTACTCTGGT AAAGTCTTTA TCCTCAGGAT   1370
GCAAGGATAC CACCCTCTTC CTGTGGAAAG TGTCGAATCA CATGCAGAGC TCTAAGTCTT   1430
     ▽
TCAGTTACTT TGGAGTGCAG AACCATTTCA Ggtaaggcca aatattttaa acattagtat   1490
aggaaattag agggctcttt agtctgtgtg tgcatgagaa gtaaaattgc acgagaagca   1550
atttatgtaa aatttcgctt aggaaacatt gttttggtag gttagtagta tggtgtgtat   1610
ttcccagaaa attcagtgcc gtgagtatta cctttagtta agcatcttag aaatagtagc   1670
tcttattgtt tatggctaag tcagaaatac tacccctcaaa ttctatgtga ccctagttat   1730
actgttgagc ctttctgtgc ctctgtgcct tcatccttga atcggggata atatacttac   1790
ctcctaaggt tattgtaagg attaaatgca tgtagtataa ataaagagct gagaacaatg   1850
catggcgtaa agtgataggt attattatat gttttgttg gctgttgatt gaaggtgttt   1910
gctgttttgg gggtgtcctt taatagagta acttggtact gtggaaatag catgattgtg   1970
agcaaaagaa tcagatggtg gtggctgcag acttgctgt tcccttcttg actgttggtt   2030
atagccaatg cagggtaagt tataaagtca agagcagagc cgttttcaca atggacattg   2090
ctttgtgatg tctgtgagct tgaatgtgag aatgattatt ttaattctct atgtaaagac   2150
tttaaagtat tggctattcg gtagcttgat ttctctgtaa tctcatgctt taaactgaga   2210
gtggaaaatc aataaagcaa aagcatgagg ccacgcagtg tagaatgagt gtcttttcac   2270
cacgtaggga aatctgtagt cctaagaaaa gagggagtga gaattctggc gaaaagattg   2330
tgcctctgca caaagtgcag gatcccaggg ttcagtacag gcgcgaacgc tcctgtgtgt   2390
                                          Met
tgaccacact cccacggttg cttttttagA CATGCTGAGG GGGACTCTAC TGTGCGCGGT   2450
```

FIG. 5A

```
GCTCGGGCTT CTGCGCGCCC AGCCCTTCCC CTGTCCGCCA GCTTGCAAGT GTGTCTTCCG  2510
GGACGCCGCG CAGTGCTCGG GGGGCGACGT GGCGCGCATC TCCGCGCTGG GCCTGCCCAC  2570
CAACCTCACG CACATCCTGC TCTTCGGAAT GGGCCGCGGC GTCCTGCAGA GCCAGAGCTT  2630
CAGCGGCATG ACCGTCCTGC AGCGCCTCAT GATCTCCGAC AGCCACATTT CCGCCGTTGC  2690
CCCCGGCACC TTCAGTGACC TGATAAAACT GAAAACCCTG AGGCTGTCGC GCAACAAAAT  2750
CACGCATCTT CCAGGTGCGC TGCTGGATAA GATGGTGCTC CTGGAGCAGT TGTTTTTGGA  2810
CCACAATGCG CTAAGGGCA TTGACCAAAA CATGTTCAG AAACTGGTTA ACCTGCAGGA  2870
GCTCGCTCTG AACCAGAATC AGCTCGATTT CCTTCCTCCC AGTCTCTTCA CGAATCTGGA  2930
GAACCTGAAG TTGTTGGATT TATCGGGAAA CAACCTGACC CACCTGCCCA AGGGGTTGCT  2990
TGGAGCACAG GCTAAGCTCG AGAGACTTCT GCTCCACTCG AACCGCCTTG TGTCTCTGGA  3050
TTCGGGGCTG TTGAACAGCC TGGGCGCCCT GACGGAGCTG CAGTTCCACC GAAATCACAT  3110
CCGTTCCATC GCACCCGGGG CCTTCGACCG GCTCCCAAAC CTCAGTTCTT TGACGCTTTC  3170
GAGAAACCAC CTTGCGTTTC TCCCTCTGC GCTCTTTCTT CATTCGCACA ATCTGACTCT  3230
GTTGACTCTG TTCGAGAACC CGCTGGCAGA GCTCCCGGGG GTGCTCTTCG GGAGATGGG  3290
GGGCCTGCAG GAGCTGTGGC TGAACCGCAC CCAGCTGCGC ACCCTGCCCG CCGCCGCCTT  3350
CCGCAACCTG AGCCGCCTGC GGTACTTAGG GGTGACTCTG AGCCGCGGC TGAGCGCGCT  3410
TCCGCAGGGC GCCTTCCAGG GCCTTGGCGA GCTCCAGGTG CTCGCCCTGC ACTCCAACGG  3470
CCTGACCGCC CTCCCCGACG GCTTGCTGCG CGGCCTCGGC AAGCTGCGCC AGGTGTCCCT  3530
GCGCCGCAAC AGGCTGCGCG CCCTGCCCCG TGCCCTCTTC CGCAATCTCA GCAGCCTGGA  3590
GAGCGTCCAG CTCGACCACA ACCAGCTGGA GACCCTGCCT GGCGACGTGT TTGGGGCTCT  3650
GCCCCGGCTG ACGGAGGTCC TGTTGGGGCA CAACTCCTGG CGCTGCGACT GTGGCCTGGG  3710
GCCCTTCCTG GGGTGGCTGC GGCAGCACCT AGGCCTCGTG GGCGGGGAAG AGCCCCACG  3770
GTGCGCAGGC CCTGGGGCGC ACGCCGGCCT GCCGCTCTGG GCCCTGCCGG GGGGTGACGC  3830
CGAGTGCCCG GGCCCCCGGG GCCCGCCTCC CCGCCCCGCT GCCCACAGCT CCTCGGAAGD  3890
CCCTGTCCAC CCAGCCTTGG CTCCCAACAG CTCAGAACCC TGGGTGTGGG CCCAGCCGGT  3950
GACCACGGGC AAAGGTCAAG ATCATAGTCC GTTCTGGGGG TTTTATTTTC TGCTTTTAGC  4010
TGTTCAGGCC ATGATCACCG TGATCATCGT GTTTGCTATG ATTAAAATTG GCCAACTCTT  4070
                                        STOP
TCGAAAATTA ATCAGAGAGA GAGCCCTTGG GTAAACCAAT GGGAAAATCT TCTAATTACT  4130
TAGAACCTGA CCAGATGTGG CTCGGAGGGG AATCCAGACC CGCTGCTGTC TTGCTCTCCC  4190
TCCCCTCCCC ACTCCTCCTC TCTTCTTCCT CTTCTCTCTC ACTGCCACGC CTTCCTTTCC  4250
CTCCTCCTCC CCCTCTCCGC TCTGTGCTCT TCATTCTCAC GGGCCCGCAA CCCCTCCTCT  4310
CTCTGTCCCC GCCCGTCTCT GGAAACTGAG CTTGACGTTT GTAAACTGTG GTTGCCTGCC  4370
TTCCCAGCTC CACGCGGTGT GCGCTGACAC TGCCGGGGGG CTGGACTGTG TTGGACCCAT  4430
CCTTGCCCCG CTGTGCCTGG CTTGGCCTCT GGTGGAGAGA GGGACCTCTT CAGTGTCTAC  4490
TGAGTAAGGG GACAGCTCCA GGCCGGGGCT GTCTCCTGCA CAGAGTAAGC CGGTAAATGT  4550
TTGTCAAATC AATGCGTGGA TAAAGGAACA CATGCCATCC AAGTGATGAT GGCTTTTCCT  4610
GGAGGGAAAG GATAGGCTGT TGCTCTATCT AATTTTTTGT TTTTGTTTTT GGACAGTCTA  4670
GCTCTGTGGC CCAGGCTGGC GTGCACTGGG CCGTCTCAGT TCACTGCAGC CTCCGCCCTC  4730
CAGGTTCAAG TGATTCTCAT GCCTCAGCGT TCTGAGTAGC TGGGATTAGA GGCGTGTGCC  4790
ACTACACCCG GCTAATTTTT GTACTTTTTA AAGTAGAGAC GGGCTTTGCC ATATTGGCCT  4850
GGCTGATCTC AAACTCCTGG TCTTGAACTC CTGGCCACAA GTGATCTGCC CGCCTTAGCC  4910
TCCCAAAGTG CTGGGATTAC AGGCGCAAGC CACTACACCT GCCCTCTTCA TCGAATTTTA  4970
TTTGAGAAGT AGAGCTCTTG CCATTTTTTC CCTTGCTCCA TTTTTCTCAC TTTATGTCTC  5030
TCTGACCTAT GGGCTACTTG GGAGAGCACT GGACTCCATT CATGCATGAG CATTTTCAGG  5090
ATAAGCGACT TCTGTGAGGC TGAGAGAGGA AGAAAACACG GAGCCTTCCC TCCAGGTGCC  5150
CAGTGTAGGT CCAGCGTGTT TCCTGAGCCT CCTGTGAGTT TCCACTTGCT TTACATCCAT  5210
GCAACATGTC ATTTTGAAAC TCGATTGATT TGCATTTCCT GGAACTCTGC CACCTCATTT  5270
CACAAGCATT TATGGAGCAG TTAACATGTG ACTGGTATTC ATGAATATAA TGATAAGCTT  5330
```

FIG. 5B

```
GATTCTAGTT CAGCTGCTGT CACAGTCTCA TTTGTTCTTC CAACTGAAAG CCGTAAAACC 5390
TTTGTTGCTT TAATTGAATG TCTGTGCTTA TGAGAGGCAG TGGTTAAAAC ATTTTCTGGC 5450
GAGTTGACAA CTGTGGGTTC AAATCCCAGC TCTACCACTT ACTAACTGCA TGGGACTTTG 5510
GGTAAGACAC CTGCTTACAT TCTCTAAGCC TTGGTTTCCT GAACCTTAAA ACAGGATAAC 5570
ATAGTACCTG CTTCATAGAG TTTTGTGAGA ATTAAAGGCA ATAAAGCATA TAATGACTTA 5630
GCCCAGCGGC CTGCAGACAA TACATGTTAA TGAATGTTAG CTATTATTAC TAAAGATGAG 5690
CAATTATTAT TGGCATCATG ATTTCTAAAG AAGAGCTTTG AGTTGGTATT TTTCTCTGTG 5750
TATAAGGGTA AGTCCGAACT TTCTCATACT GGAGGTTACA TTCACATCAG TCTGTCTTCC 5810
CCTGCGGATG GCCTCAGCCC TGGGTGGCCA GGCTCTGTGC TCACAGTCCA GAGCAATGGA 5870
TCCTCCAACA CCACCAGGTG GATGTGGAGC AGGAGAGCTG GATCGTGGCA TTTGTTTCTG 5930
GGTTCTGCAG TTGGGAGTTG GTTTCTGGGT TCTCCATTGG TCTACTTGTC TAGTCCCATA 5990
CCAGACTCAC GGTCTCCATT ATTGGAGCTT TAATAATTTT TGGTATAGGG TCATCTCTCC 6050
ACCTTGTTTT TCTTCTATTC TTGGTTCTTT GCAATTCTAT GAATATTTCA GGGTCAGCAT 6110
GTCAACTCCA TTGAAAAACC CTGCTGGGAT TTTAATAGAA CTTACAGCTC ACGCCTGTAA 6170
TCCCAGCACT TTGGGAGGCT GAGGTGGGTG GATCACAGGT CAGGAGTTTG AGAACAGCTG 6230
GCCAAGATGG TGAAACCCCG TCTCTACTAA AAATACAAAA ATTAGCTGGG TGCGGTGGCA 6290
GGTGCCTGTA GTCCCAGCTA CTTGGGACAC CGAGGCAGGA GAATCACTTG AACCCGGGAG 6350
GCGGAGGTTG CAGTGAGCCG AGATCGTGCC ACTGCACTCT AGCCTGGGCG ACAGAGCGAG 6410
ACTCCATCTC AAAAAAAAAG AAAAAGAAAA TTGCAGTAAA TTTAAAACTA ATTTGGGGAA 6470
GAATCTGTAT TTTTACAATA CCTAGTGTTC TTGCCAGTAA GCATGGTTCA TCTTCCCATT 6530
TATTTACGTC ATTTTAAATC TTTCAGTGAT GTTTTAGAAT TTTTTTTATA AAAACCTTCA 6590
CTATAAGAAC AGAAAACCAA ACACCGCATG TTCTCACTCA TAGGTGGGAA TTGAACAATG 6650
AGAACACTTG GACACAGGGC GGGGAACGTC ACACGCCTGG ACTGTTGGGG GGGTGGCTGG 6710
GAGAGGGATA GTGTTAGGAG AAATACCTAA TGTAAATGAC GAGTTAATGG TGCAGCCAAC 6770
CAACCTGGCA CATGTATTCA TATGTAACAA ACCTGCACGT TGTGCACATG TACCCTAGAA 6830
CTTAAAGTAT ATTAAAAAAA GAAACCTTGG CACTGATTTT GTTAGATTTA TTCCTAGGTA 6890
TCCTTCCTCT TTTTTGATTT GTCATTGCTA TTGTAGATGG CATCTTTTTA AAAGTTATA 6950
TTTTCTAAAG CAAAAAATAA AAAAGTTGT ATTTCTAATT TTTATTACCA ATATATAAGA 7010
ATGTAATTTA TTTTTACATA ATTATCTTAT GTCTAGTAAT AATTCTGATA ATTTGCTTCT 7070
TCCTATTAAA ACCTTACACC CATTATTGAT TTATTTTTCT GTTTTAAAAT ATCTTCCTGC 7130
ACTGGCTAAA ACCTCCACTA TAATGTTGAG CAGAACAGTG AGGCATCCTT AGAACTATCT 7190
TGGTTGCAAA GGGTAGGTCT CTAATGTTTC ATCAATAAAT GTGATGTTTC TAGTCTGAGT 7250
TTGCTAAGTA TATTTTAAAA TAATCAGTAA AGTTAGATTT TATCCATTTT TATCTTAACT 7310
ATTGAGATGC TCATATCATT TTTCTTCTTC AATGTGTTAA AATGGTGAAT AAATTTATAG 7370
ATTTTGGAAA AGTAAATTCA TTCTTGCATT CCCGAAGTAA ACCAAGCCAT GCTATGTGTA 7430
TTTAAAATAT ATTGCTGAAT TC-3'                                      7452
```

LEU-RICH REPEATS

```
 1 - G R G V L Q S Q S F S G M T V K L Q R L M I S D S
 2 - H I G S V A P G T F S D K L I V K L L Q E L R F A S D R N
 3 - K I T H L P G A N S L L D K M L V L L L Q E L L A D L H Q N
 4 - A L R G I D Q N S M F Q T K L V E L L Q K L L D N S H N
 5 - Q L D F L P A K S L F D T G N L E A L L K E L L D L H G N
 6 - N L D T H S L P A G G L L T G N A G L N K L L E T L L L Q T N
 7 - R L V S L D K S G G L L A S R L P N G L L S T L F T W R L S R N
 8 - H I R S I A P G A F D R L H P N L L S T L L T W S F R E N
 9 - H L A F L P S A V L F D L G R L S M H G L L Q L L Y T L F N T N
10 - P L A E L P S G V A F F H E N L L G N L L L L L V T S F N T
11 - Q L R S L P A A A F F R G R L S G R L L E Y L L V T H R D S
12 P R L S T A A L P Q G A F F Q G E L S G R L Q R E T V A S Q H R D N
13 - G L S T A A L P D G L L R G N A L L G G K L L R E T V S Q L H R D G N
14 - R L R A T L P R G D L F R G N A L L S P L L R E V V Q L H H N
15 - Q L E T L P P G D V F R G A L L L L T E V L H H N
```

CONSENSUS SEQUENCE: X L X X L P X X L F X X L X X L X X L X L X X N

FIG. 6.

| | $P_7$ | $P_6$ | $P_5$ | $P_4$ | $P_3$ | $P_2$ | $P_1$ | $P'_1$ | $P'_2$ | $P'_3$ | $P'_4$ |
|---|---|---|---|---|---|---|---|---|---|---|---|
| GPV    | A | E | C | P | G | P | R | G | P | P | P |
| Fg Aα 1 | A | E | G | G | G | V | R | G | P | R | V |
| Fg Aα 2 | G | G | V | R | G | P | R | V | V | E | R |
| Fg Bβ  | E | G | F | F | S | A | R | G | H | R | P |
| F XIII | E | L | Q | G | V | P | R | G | V | D | L |
| CGβ    | R | L | P | G | C | P | R | G | V | N | P |

FIG. 7.

PLATELET GLYCOPROTEIN V GENE AND USES

This application is a Continuation-in-Part of U.S. application Ser. No. 08/089,455 filed Jul. 9, 1993 now abandoned.

BACKGROUND OF THE INVENTION

Platelets arise from the fragmentation of megakaryocytes, which are large polyploid bone marrow cells produced by several cycles of chromosomal duplication without cytoplasmic division (Handin (Wilson et. al., eds) in *Harrison's Principles of Internal Medicine,* 12th edition (1991)). Once free of the marrow space, approximately ⅔ of the platelets circulate freely, while approximately ⅓ are sequestered in the spleen. Circulating platelets last for 7 to 10 days, after which they are removed by phagocytic cells. A decrease in platelet mass stimulates megakaryocytopoiesis, resulting in an increase in the number, size and ploidy of the megakaryocytes.

Platelet receptors which mediate platelet adhesion and aggregation are located on the two major platelet surface glycoprotein complexes. These complexes are the glycoprotein Ib-IX complex which facilitates platelet adhesion by binding von Willebrand factor (vWF), and the glycoprotein IIb-IIIa complex which links platelets into aggregates by binding to fibrinogen. Patients with the Bernard-Soulier syndrome, a congenital bleeding disorder, show deficient platelet adhesion due to a deficiency in the glycoprotein Ib-IX complex which binds VWF, mild thrombocytopenia, and large lymphocoid platelets.

Glycoprotein v (GPV) is a major (≈12,000 molecules/platelet), heavily glycosylated platelet membrane protein (Mr 82,000) (Modderman et. al. *J. Biol. Chem.* 267:364–369). Earlier reports showing that GPV was a peripheral protein (Berndt and Phillips *J. Biol. Chem.* 256:59–65) were presumably due to the release of GPV from the membrane by calpain during the purification procedure. Exposure of platelets to thrombin liberates a 69 kDa soluble fragment termed GPVfl (Phillips and Poh-Agin, *Biochem. Biophys. Res. Commun.* 75:940–947). This, and its absence in the Bernard-Soulier syndrome (Clemetson et. al. *J. Clin. Invest.* 70:304–311 (1982); Nurden et. al., *J. Clin. Invest.* 67:1431 (1981); Berndt et. al., *Blood* 62:800–807 (1983)), led to the suggestion that GPV may be involved in the thrombin-induced activation response (Berndt and Phillips L. *J. Biol. Chem* 256:59–65 (1981)). Recent experiments show that GPV can interact non-covalently with the GPIb-IX complex (Modderman et. al. *J. Biol. Chem.* 267:364–369 (1992)), a complex formed by the non-covalent association of GPIb (consisting of GPIbα, a 145 kDa protein, disulfide linked to GPIbβ, a 24 kDa protein) with GPIX (a 22 kDa protein). The binding sites for von Willebrand factor and for thrombin on the GPIb-IX complex have been localized on GPIbα (Wicki and Clemetson *Eur. J. Biochem.* 153:1–11 (1985); Vicente et. al., *J. Biol. Chem.* 265:274–280 (1990)). Since thrombin is now known to activate platelets by cleaving the thrombin receptor (Vu et. al., *Cell* 64:1057–1068 (1990)), a G-protein coupled receptor, it is unknown whether thrombin cleaves GPV incidently as a consequence of thrombin binding to GPIbα, or whether this cleavage has a physiological role.

The amino acid sequences of GPIbα, GPIbβ, and GPIX have been deduced from their cDNA and genomic sequences (Lopez et. al., *Proc. Natl. Acad. Sci. USA* 84:5614–5619 (1987); Wenger et. al., *Biochem. Biophys. Res. Commun.* 156:389–395 (1988); Lopez et. al., *Proc. Natl. Acad. Sci. USA* 85:2135–2139 (1988); Hickey, et. al., *Proc. Natl. Acad. Sci. USA* 86:6733–6777 (1989); Hickey and Roth *J. Biol. Chem* 268:3438–3443 (1993)). Analysis of the primary amino acid sequence of GPIBα, GPIBβ, and GPIX has revealed a common evolutionary origin for the three proteins, as they contain one or more homologous 24 amino acid leucine-rich domains. These domains are also found in a large family of leucine-rich glycoproteins (LRG) including leucine-rich α2 GP, proteoglycan core, fibromodulin, human lutropin-chorio gonatropin receptor and RNAse inhibitor, and toll protein and chaoptin found in Drosophila (reviewed in Roth *Blood* 77:5–19 (1991)). Recently, analysis of partial peptide sequences obtained from purified platelet GPV suggested that GPV is also a member of the LRG family (Shimomura et. al., *Blood* 75:2349–2356 (1990); Roth et. al., *Biochem. Biophys. Res. Commun.* 170:153–161 (1990)).

GPV is a very specific marker for the megakaryocytic cell lineage. A monoclonal antibody specific for GPV (SW16) was recently shown to bind exclusively to platelets (Modderman et. al., *J. Biol. Chem.* 267:364–369 (1992)). SW16 did not bind to red cells, leukocytese endothelial cells, or cell lines such as HEL or MEG-01 which are known to express platelet megakaryocyte markers.

SUMMARY OF THE INVENTION

The invention comprises an isolated DNA construct comprising the polynucleotide sequence of the glycoprotein v gene, including the polynucleotide sequence which has the sequence shown in FIGS. 5A–C. The polynucleotide sequence encodes a GPV polypeptide, including the amino acid sequence as shown in FIG. 5D. The polynucleotide sequence may lack introns, and may incorporate a heterologous promoter operably linked to the polynucleotide sequence which is capable of directing expression in a prokaryote or in a eukaryote.

The invention further comprises a DNA construct wherein the polynucleotide sequence encodes a full length glycoprotein V polypeptide.

The present application includes prokaryotic or eukaryotic a cell containing a glycoprotein v DNA construct.

The present application further provides for a pharmaceutical composition comprising a pharmaceutically acceptable carrier and a glycoprotein v polypeptide. The polypeptide may have the sequence shown in FIG. 5D.

A further understanding of the nature and advantages of the invention will become apparent by reference to the remaining portions of the specification and drawings.

BRIEF DESCRIPTION OF THE DRAWINGS

(a) The top line represents the coding region (open bar) and 5'-untranslated sequence (hatched bar) for a platelet GPV cDNA with a partial restriction map. The cloning strategy is indicated below. Overlapping clones (i to vi) covering 1,199 bp of cDNA were obtained after PCR amplification of platelet mRNA The oligonucleotide primers used for the amplification are indicated and the corresponding sequences are listed in Table I. The GPV 8.1 kb genomic fragment (1) was obtained after screening a human genomic library in the λFix vector with a 748 bp $^{32}$P-labelled GPV cDNA probe (indicated in (a) by a broken line). The top line is a partial restriction map of the gene. Exons are boxed: the open box represents the coding sequence, the hatched box represents the 5'-untranslated sequences, and the shaded box represents the 3'-untranslated region. The vertical arrow indicates the beginning of the genomic sequence reported in FIGS. 5A–C. The open arrowhead indicates the 5'-end and the closed arrowhead indicates the 3'-end of the partial platelet cDNA obtained by PCR. A sequence with perfect consensus for a TATA box is indicated. The closed circles indicate AATAAA consensus sequences for polyadenylation signals. The restriction sites are indicated as follows A, Acc I; Be Bam HI; E, Eco RI; K, Ksp I; P, Pst I; Se Sac I; X, Xho I. FIG. 2A shows that platelet (PLT) and megakaryocyte (MGK) RNA were amplified with a mixture of two GPV primer pairs (nt 3,010–3,589 and 2,675–2,877) generating bands of 579 bp and 202 bp. FIG. 2B shows that HEL cells with (HEL+ PMA) or without (HEL) stimulation with phorbol ester, HL60, and platelet (PLT) RNA were amplified with a GPV primer pair (nt 3,091–3,589) generating a 498 bp band.

FIGS. 5A–C (SEQ.ID.NO. 1) and 5D (SEQ.ID.NO. 2): Sequence of the human GPV gene FIG. 5A–C and deduced amino acid sequence FIG. 5D of the GPV protein. The GPV genomic sequence (SEQ.ID.NO. 1) FIGS. 5A–C are shown in the 5'- to 3'-orientation with the single intron sequence of 958 bp shown in lower case letters. The gt/ag donor and acceptor sites are in bold characters. Consensus sequences for putative cis-acting promoter elements are indicated as shaded areas. The closed circle indicates a possible Cap site. The ATG translation start and the in-frame TAA stop codon are boxed. The open arrowhead (nt 1,433) and closed arrowhead (nt 3,589) indicate the 5'- and 3'- end, respectively, of the partial cDNA sequence obtained by PCR amplification of platelet RNA. Two Alu repeats, nt 598–886 and nt 6,133–6,440, are underlined. Possible polyadenylation signal sequences (nt 5,610, nt 6,966, nt 7,224 and, nt 7,358) are double underlined. The GPV amino acid sequence FIG. 5D (SEQ.ID.NO. 2), indicated in single letter code, was deduced after translation of the cDNA and genomic sequences. The putative signal peptide is underlined. The putative transmembrane domain is double underlined. Cysteine residues are circled. Potential N-linked glycosylation sites in the extracellular domain are indicated by a vertical arrowhead. N-glycosylation sites that had been identified by protein sequencing are indicated by a star. Internal peptide sequences that were obtained from purified platelet GPV (20, 21), indicated in italics, are underlined by a broken arrow. Differences between the DNA-derived and internal peptides sequences are indicated in parenthesis as lower case letters. (x) indicate a residue which had not been determined in the original peptide sequence.

FIG. 6: Alignment of the 15 tandem Leu-rich repeated structures for platelet GPV (SEQ.ID.NOs. 22–36). The alignment spans the sequences between residues 61 and 421 of the protein. Identical residues among the 15 segments are boxed. An overall consensus sequence for the GPV repetitive motifs is presented (SEQ.ID.NO. 37).

FIG. 7: comparison of the GPV thrombin cleavage site to other thrombin substrates. The GPV sequence around the RG thrombin cleavage peptide bond (SEQ.ID.NO. 38) was aligned with sequences of human fibrinogen (Fg) Aα (SEQ.ID.NOs. 39 and 40) and Bβ (SEQ.ID.NO. 41) chains, to human plasma factor XIII (FXIII) (SEQ.ID.NO. 42), and to human chorionic gonatropin β-subunit (CGβ) (SEQ.ID.NO. 43). Amino acid residues identical to GPV are boxed.

DETAILED DESCRIPTION OF SPECIFIC EMBODIMENTS

Figure 1:
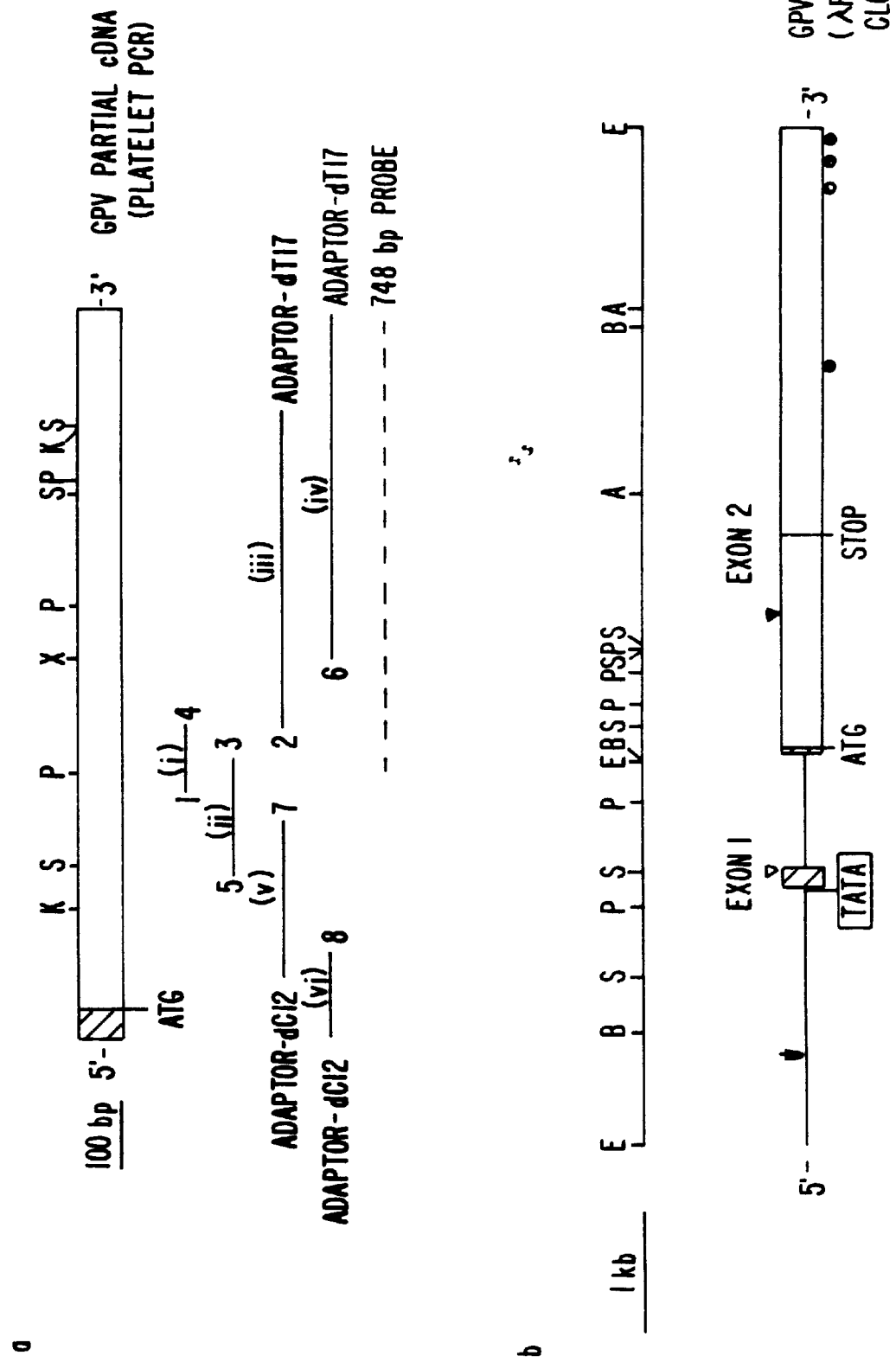
FIG. 1 part (a) illustrates the cloning, sequencing strategy, and restriction map of a partial human platelet GPV cDNA, whereas part (b) illustrates the complete human GPV gene.

The present invention provides the primary structure of the human GPV gene and the structure of the GPV protein. The single-copy gene for GPV is contained within 6.5 kb of genomic sequence, and has a simple structure with a single intron of 958 bp in the 5'-untranslated sequence; the coding sequence is contained within a single exon. The promoter region contains a canonical TATA box, and putative GATA, Ets-1, and Spl cis-acting elements. RT-PCR analysis on RNAs from cells of different hematopoietic origins revealed that GPV was specifically transcribed from platelets and from calls of the megakaryocytic lineage (megakaryocytese HEL cells). A single transcript of 405 kb for GPV was detected in human platelets by Northern blot analysis, and the entire amino acid sequence of GPV was deduced from the cDNA and genomic sequences.

Mature GPV is composed of 543 amino acids which contain a single transmembrane domain, a short cytoplasmic domain (16 residues) and a large extracellular domain with 8 potential N-glycosylation sites. Analysis of the extracellular domain revealed the presence of 15 tandem Leu-rich repeats of 24 amino acids with homology to GPIbα, and identified a cleavage site for thrombin near the C-terminus with homology to the Aα chain of fibrinogen.

The predicted amino acid sequence of GPV accounts for the known features of the protein First, it contains with one exception (peptide M4 Shimamura et. ala. *Blood*

75:2349–2356 (1990) all of the partial peptide sequences which had been reported for purified platelet GPV (FIGS. 5A–C). Second, the predicted molecular weight of the polypeptide chain of 59,276 Da agrees with the 60 kDa value determined after SDS-PAGE analysis of the deglycosylated protein. Third, the predicted amino acid composition is very similar to that reported for purified GPV when the data are corrected for the 59,276 molecular mass. Fourth, the LRG repeats in GPV display significant similarity to those found in the subunits of the GPIb-IX complex, which GPV associates with in platelets. Finally, the translated protein contains a thrombin cleavage recognition site at a position which would generate a soluble cleavage fragment of the size of GPVfl, a fragment known to be generated after platelet treatment with thrombin (Phillips and Poh-Agin, Biochem. Biophys. Res. Commun. 75:940–947 (1977); Mosher et. al., Blood 53:437–445 (1979)).

Analysis of the deduced primary amino acid sequence revealed several distinctive features for GPV. The protein contains an N-terminal signal peptide with a consensus cleavage site (Von Heijne, J. Mol. Biol. 173:243–251 (1984)) at a Gln residue. N-terminal glutamines are often cyclized to pyroglutamic acids, explaining the N-terminal blockade consistently observed with purified GPV. A second hydrophobic domain was located at the C-terminus of the protein suggesting that GPV is a transmembrane protein. This agrees with data showing that GPV was found in the hydrophobic phase of a Triton X-114 phase partition (Bienz et. al., Blood 68:720–725 (1986)). GPV contains 8 potential N-glycosylation sites, located on the extracellular domain. The presence of O-linked carbohydrates and sialic acid has been suggested based upon a 10 kDa molecular weight reduction following neuraminidase treatment (Zafar and Walz Thromb. Res. 53:31–44 (1989)). One short region in the C-terminal region contains two Ser-rich segments and could contain O-linked sugars, but it is probable that the bulk of the carbohydrates are represented by N-sugars due to the observed 20,000 Da apparent molecular weight drop after treatment of GPV by N-glycanase (Zafar and Walz Thromb. Res. 53:31–44 (1989)). GPV has a very short intracellular domain which contains no potential phosphorylation site as it lacks any Tyr, Ser, or Thr residues. The C-terminal intracellular domain also lacks an unpaired cysteine residues which is a site for acylation by fatty acids which is found in GPIbβ and GPIX (Lopez et. al., Proc. Natl. Acad. Sci. USA 85:2135–2139 (1988); Hickey et. al. Proc. Natl. Acad. Sci. USA 86:6773–6777 (1989)). Thus, most of the polypeptide chain (92%) is exposed to the outside of the platelet. This is consistent with the observed release of a GPV fragment slightly smaller (80 kDa) than intact membrane bound GPV after treatment of platelets with calpain (Bienz et. al., Blood 68:720–725 (1986)). This observation shows that the cleavage site for calpain must lie in a region between the last C-terminal N-glycosylation site and the transmembrane domain. The eight cysteine residues are not evenly distributed in the protein: four are clustered in the H-terminal portion, and four are in the region between the Leu-rich domains and the membrane in the C-terminal part of the extracellular segments The absence of an apparent molecular weight change upon reduction (Berndt and Phillips J. Biol. Chem. 256:59–65 (1981)) suggests that all the disulfide bonds are formed over short distances. The absence of cysteines in the middle portion of the molecule indicates that this region is susceptible to enzymatic cleavages accounting for its sensitivity to various enzymes such as calpain, chymotrypsine elastase and thrombin.

Analysis of the peptide sequence for a putative thrombin cleavage site revealed the presence of an Arg-Gly motif at position 476–477. This appears to be the actual cleavage site based on the following observations: firsts the estimated molecular weight of the fragment liberated by thrombin would be 67,613 Da after correction for the presence of seven N-glycosylation sites, which is similar to the apparent molecular weight of the GPVfl fragment. Second, the amino acid sequence around the Arg-Gly peptide bond displayed significant similarity to sequences around known thrombin cleavage sites (Muszbek and Laki et. al., (R. Nachovich, ed) in The Thrombin pp 83–90, CRC Press, Boca Raton, Fla. (1984)), and most notably the Aα chain of fibrinogen. The sequence is also similar to other thrombin substrates where a high incidence of proline residues occur at the P2 subsite. Finally, the sequence immediately after the RG peptide corresponds to the N-terminal sequence of a peptide obtained after thrombin cleavage of purified GPV (Shimomura et. al., Blood 75:2349–2356 (1990); Roth et. al., Biochem Biophys. Res. Commun. 170:153–161 (1990)).

The prior art suggests that GPV has a high affinity binding site for thrombin. The GPVfl fragment is generated at concentrations of thrombin in the nM range: α-thrombin cleaves 100% of platelet GPV at concentrations less than 30 nM (Jandrot-Perrus et. al. Thromb. Haemostas. 58:915–920 (1987)). In addition, direct interaction of GPV with thrombin was demonstrated by the selective retention of purified GPV on a thrombin-Sepharose column which could then be eluted with heparin (Bienz et. al., Blood 68:720–725 (1986)). Other examples of platelet proteins known to interact with thrombin with high affinity are the newly cloned thrombin receptor, and GPIBα (Vu, et. al., Cell 64:1057–1068 (1991); Lopez et. al., Proc. Nat. Acad. Sci. USA 84:5614–5619 (1987); De marco et. al., J. Biol. Chem. 266:23776–23783 (1991)).

Figure 8:
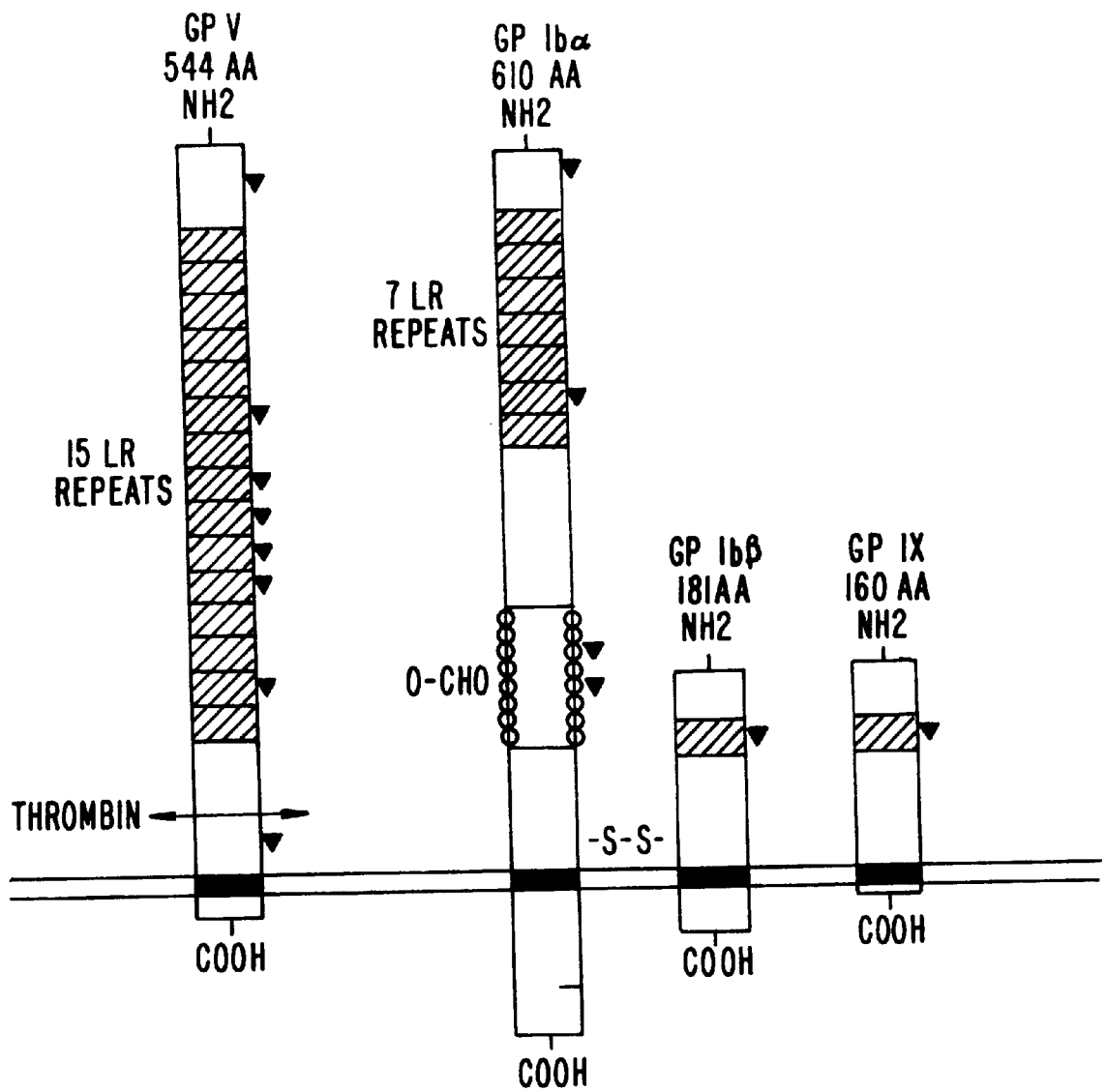
FIG. 8 Schematic representation of the GPV protein inserted in the platelet plasma membrane in comparison with the GPIb-IX complex. The proteins depicted as bars, are oriented with their NH$_2$— and COOH-termini oriented toward the outside and inside of the cell, respectively. Numbering of amino acids for the mature proteins is indicated. The transmembrane domains are represented as solid rectangles. The Leu-rich (LR) repetitive domains are represented as hatched rectangles. N-glycosylation sites are indicated as solid triangles. GPIbα contains a region rich in O-linked sugars (O—CHO) and is linked to GPIbβ by a disulfide (S—S) bond. The location of the thrombin cleavage site in GPV is indicated by a double-headed arrow.

A distinctive feature of GPV is that it has the highest leucine content (comprising 20% of the amino acids) of the known platelet proteins. Most of the leucine residues in GPV are contained within 15 tandem Leu-rich repeats of 24 amino acids similar to repeats found in the LRG family of proteins (Roth, Blood 77:5–19 (1991)), and most noticeably to platelet GPIBα (7 LRG repeats), GPIbβ (1 LRG repeat), and GPIX (1 LRG repeat) (FIG. 8). The LRG domains, at least in some members of the family, mediate protein-protein, cell-cell, or cell-matrix interactions. For example, proteoglycan II (Krusius et. al., Proc. Natl. Acad. Sci. USA 83:7683–7687 (1986)) and fibromodulin (Hashimoto et. al., Cell 52:269–279 (1988)) bind to a specific type of collagen, and Drosophila chaoptin (Reinke et. al., Cell 52:291–301 (1988)) and toll (Oldberg et. al., EMBO J. 8:2601 (1989)) proteins orient cells during morphogenesis and embryogenesis, respectively.

Analysis by the sensitive RT-PCR amplification technique revealed the presence of GPV mRNA in platelets and megakaryocytes. A GPV transcript was also detected in HEL cells which were upregulated after treatment with a phorbol ester which is a known inducer of megakaryocyte differentiation in HEL cells. RT-PCR analysis did not reveal GPV mRNA in non megakaryocytic cells such as leukocytes, endothelial cells, HL60 and U937 cells. Northern analysis revealed a transcript of approximately 4.5 kb in platelets and also revealed a positive band of lower size in lymphocytes. Further analysis is needed to identify the nature of this transcript, but it could represent some related gene revealed by the long exposure times necessary to detect the minute amounts of mRNA present in platelets. The restricted distribution to platelets, coupled to a high sensitivity to thrombin cleavage makes GPV a useful marker for megakaryocytopoiesis and for the detection of thrombin dependent platelet activation in thrombotic or prethrombotic states.

The present invention demonstrates that GPV is the product of a single gene. The GPV gene is interrupted by a single intron within the 5'-untranslated region with consensus GT/AG donor and acceptor sites. Several observations show that the isolated genomic clone was derived from the gene for GPV. First, the genomic sequence in exon 2 agrees completely with the cDNA sequence obtained from platelet mRNA. Second, the restriction map of the isolated clone is consistent with restriction fragments identified herein by Southern analysis of human chromosomal DNA. The structure of the GPV gene is very similar to that of the GPIBα gene (Wenger et. al., *Biochem. Biophys. Res. Commun.* 156:389–395 (1988), another platelet member of the LRG family, both have a single intron in the 5'-untranslated sequence and their entire coding sequence is contained within a single exon. The sequence of the GPIX gene was recently reported (Hickey et. al., *J. Biol. Chem.* 268:3438–3443 (1993)), and was shown to contain its entire coding region in a single exon and to have its 50-non coding region interrupted by two introns. The similar exon-intron distribution for the GPV, GPIBα, and GPIX genes suggests that these genes might have a common evolutionary origin within the LRG family of proteins. Analysis of the 5'-flanking region of the GPV gene for cis-acting elements, and comparison to available sequences from other megakaryocyte specific genes revealed significant differences and similarities. Unlike the PF4 (Doi et. al., *Mol. Cell. Biol.* 7:898–904 (1987)), GPIBα (Wenger et. al., *Biochem. Biophys. Res. Commun.* 156:389–395 (1988)), GPIIb (Prandini et. al., *Biochem. Biophys. Res. Commun.* 156:595–601 (1988); Heidenreich et. al., *Biochemistry* 29:1232–1244 (1990)), and GPIX (Hickey et. al., *J. Biol. Chem.* 268:3438–3443 (1993)) genes, the GPV gene contains a perfect consensus sequence for a canonical TATA box which is found in the majority of RNA polymerase II transcribed genes. Similar with the other megakaryocyte specific genes, the GPV gene lacks a CAAT sequences and contains putative binding sites for GATA-1, Ets-11 and Sp1 transactivating factors. Recent experiments support the association of GATA and Ets-1 cis-acting sequences in megakaryocyte-specific gene expression (Lemarchandel et. al., *Mol. Cell. Biol.* 16:668–676 (1993)) while Sp1 sites interact with more ubiquitous transcription factors.

The availability of the genomic sequence for GPV is useful in the characterization of patients with Bernard-Soulier syndrome. These patients are characterized by an absence of or defects in the GPIb-IX glycoprotein complex and the GPV platelet glycoprotein. The availability of the GPV cDNA sequence allows for the assessment of the role of GPV in the correct expression of the four proteins which are deficient in the Bernard-Soulier syndrome. The demonstration of a requirement of GPV for correct and efficient formation of the GPIb-IX complex indicates that a defect in the gene for GPV can cause certain types of Bernard-Soulier syndrome. The availability of the genomic sequence allows for the detection of possible alterations in the GPV gene of such patients.

As used herein the terms "GPV" or "glycoprotein V" refer to polypeptide sequences at least substantially similar to GPV sequence disclosed here. The terms also specifically refer to fragments such as GPVfl as well as the full-length protein. Typically polypeptides will consist of from about 50 to about 560 residues, preferably between about 75 and 500, more preferably between about 100 and about 480 residues. The GPV sequences of the present invention can be readily designed and manufactured utilizing various recombinant DNA techniques well known to those skilled in the art and described in detail, below. For example, the chains can vary from the naturally-occurring sequence at the primary structure level by amino acid insertions, substitutions, deletions, and the like. These modifications can be used in a number of combinations to produce the final modified protein chain.

The amino acid sequence variants of GPV can be prepared with various objectives in mind, such as facilitating purification and preparation of the protein. The modified molecules are also useful for modifying plasma half life, improving therapeutic efficacy and lessening the severity or occurrence of side effects during therapeutic use. The amino acid sequence variants are usually predetermined variants not found in nature. The variants typically exhibit the same biological activity as naturally occurring GPV, such as the ability to form complexes with GPIb-IX. However, the variants and derivatives that are not capable of binding to ligands are useful nonetheless (a) as a reagent in diagnostic assays for GPV or antibodies to GPVE (b) as agents for purifying anti-GPV antibodies from antisera or hybridoma culture supernatants when insolubilized in accord with known methods, and (c) as immunogens for raising antibodies to GPV or as immunoassay kit components so long as at least one GPV epitope remains active.

In general modifications of the gene encoding the GPV may be readily accomplished by a variety of well-known techniques, such as site-directed mutagenesis (see, Gillman and Smith, *Gene* 8:81–97 (1979) and Roberts, S. et al., *Nature* 328:731–734 (1987), both of which are incorporated herein by reference). One of ordinary skill will appreciate that the effect of many mutations is difficult to predict. Thus, most modifications are evaluated by routine screening in a suitable assay for the desired characteristic For instance, a change in the immunological character of the GPV can be detected by competitive immunoassay with an appropriate antibody. The effect of a modification on the ability of the GPV to promote platelet aggregation can be tested using in vitro assays, well known to those of skill in the art. Modifications of other properties such as redox or thermal stability, hydrophobicity, susceptibility to proteolysis, or the tendency to aggregate are all assayed according to standard techniques.

Insertional variants of the present invention are those in which one or more amino acid residues are introduced into a predetermined site in the protein and which displace the preexisting residues. For instances insertional variants can be fusions of heterologous proteins or polypeptides to the amino or carboxyl terminus of GPV. Such fusion proteins can be used to facilitate purification of the encoded protein.

Immunogenic fusions may also be produced by crosslinking in vitro or by recombinant cell culture using DNA encoding an immunogenic polypeptide linked to a nucleotide sequence encoding GPV. These immunogenic fusions are useful, for instance, to raise antibodies useful in diagnostics or in purification of GPV by immunoaffinity techniques well known to the skilled artisan.

Substitutional variants are those in which at least one residue has been removed and a different residue inserted in its place. Non-natural amino acid (i.e., amino acids not normally found in native proteins), as well as isosteric analogs (amino acid or otherwise) are also suitable for use in this invention.

Substantial changes in function or immunological identity are made by selecting substitute residues that differ in their effect on the structure of the polypeptide backbone (e.g., as a sheet or helical conformation), the charge or hydrophobicity of the molecule at the target site, or the bulk of the side chain. The substitutions which in general are expected to produce the greatest changes in function will be those in which (a) a hydrophilic residue, e.g., serine or threonine, is substituted for (or by) a hydrophobic residue, e.g. leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamine or aspartine; or (d) a residue having a bulky side chain, e.g., phenylalanine, is substituted for (or by) one not having a side chain, e.g., glycine.

Substitutional variants of the subunits also include variants in which functionally homologous (having at least about 70% similarity) domains of other proteins are substituted by routine methods for one or more of the GPV domains.

Another class of variants are deletional variants. Deletions are characterized by the removal of one or more amino acid residues from the GPV sequence. Deletions of cysteine or other labile residues also may be desirable for example in increasing the oxidative stability of the protein. Deletion or substitutions of potential proteolysis sites e.g., Arg Arg, is accomplished by deleting one of the basic residues or substituting one by glutaminyl or histidyl residues.

A preferred class of substitutional or deletional variants are those involving the transmembrane region of the protein. Inactivation of the transmembrane domain, typically by deletion or substitution of transmembrane domain hydroxylation residues, will facilitate recovery and formulation by reducing its cellular or membrane lipid affinity and improving its aqueous solubility. Alternatively, the transmembrane and cytoplasmic domains can be deleted to avoid the introduction of potentially immunogenic epitopes. Inactivation of the membrane binding function is accomplished by deletion of sufficient residues (not necessarily all the residues) to produce a substantially hydrophilic hydropathy profile at this site or by substituting with heterologous residues which accomplish the same result.

A principal advantage of the transmembrane inactivated GPV is that it may be secreted into the culture medium of recombinant hosts. This variant is soluble in body fluids such as blood and does not have an appreciable affinity for cell membrane lipids, thus considerably simplifying its recovery from recombinant cell culture. Deletional variants typically substantially lack a transmembrane domain and consist essentially of the effective portion of the extracellular domain of GPV. In some circumstances, the molecule may comprise sequences from the transmembrane region (up to about 10 amino acids), so long as solubility is not significantly affected.

The transmembrane domain may also be substituted by any amino acid sequence, e.g., a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) variants these variants are secreted into the culture medium of recombinant hosts.

Glycosylation variants are included within the scope of this invention. They include variants completely lacking in glycosylation (unglycosylated) and variants having at least one less glycosylated site than the native form (deglycosylated) as well as variants in which the glycosylation has been changed. Included are deglycosylated and unglycosylated amino acid sequence variants, deglycosylated and unglycosylated subunits having the native, unmodified amino acid sequence. For example, substitutional or deletional mutagenesis is employed to eliminate the N- or O-linked glycosylation sites of the subunit, e.g., the asparagine residue is deleted or substituted for by another basic residue such as lysine or histidine. Alternatively, flanking residues making up the glycosylation site are substituted or deleted, even though the asparagine residues remain unchanged, in order-to prevent glycosylation by eliminating the glycosylation recognition site. Additionally, unglycosylated subunits which have the amino acid sequence of the native subunits are produced in recombinant prokaryotic cell culture because prokaryotes are incapable of introducing glycosylation into polypeptides.

Glycosylation variants are conveniently produced by selecting appropriate host calls or by in vitro methods. Yeast, for example, introduce glycosylation which varies significantly from that of mammalian systems. Similarly, mammalian cells from a different species (e.g., hamster, murine, insect, porcine, bovine or ovine) or tissue than the GPV source are routinely screened for the ability to introduce variant glycosylation as characterized for example by elevated levels of mannose or variant ratios of mannose, fucose, sialic acid, and other sugars typically found in mammalian glycoproteins. In vitro processing of the subunit typically is accomplished by enzymatic hydrolysis, e.g., neuraminidase digestion.

The polypeptides of the invention can consist of the full length GPV or a fragment thereof as described above. Particularly preferred polypeptides of the invention are those having a polypeptide sequence substantially identical to the sequence disclosed in FIG. 5D.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman Proc. *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.) or by inspection. These references are incorporated herein by reference.

The percentage of sequence identity between two sequences is determined by comparing two optimally aligned sequences over a window of comparison of at least 20 positions. The percentage is calculated by determining the number of positions at which the identical nucleic acid bass or amino acid residue occurs in both sequences to yield the number of matched positions, dividing the number of matched positions by the total number of positions in the window of comparison (i.e., the window size), and multiplying the result by 100 to yield the percentage of sequence identity.

The term "substantial identity" means that a polypeptide comprises a sequence that has at least 80% sequence identity, preferably 90%, more preferably 95% or mores compared to a reference sequence over a comparison window of about 20 residues to about 500 residues—typically about 50 to about 500 residues usually about 250 to 300 residues. The values of percent identity are determined using the programs above.

Another indication that polypeptide sequences are substantially identical is if one protein is immunologically reactive with antibodies raised against the other protein.

Thus, the polypeptides of the invention include polypeptides immunologically reactive with antibodies raised against GPV.

The present invention provides substantially pure preparation of GPV polypeptides, produced either by recombinant or synthetic means, or isolated from natural sources. The phrases "isolated" or "biologically pure" refer to material which is substantially or essentially free from components which normally accompany it as found in its native state. Thus, the binding domain polypeptides of this invention do not contain materials normally associated with their in situ environment, e.g., other proteins from a platelet membrane. However, even where a protein has been isolated to a homogenous or dominant band by PAGE, there can be trace contaminants in the range of 5–10% of native protein which co-purify with the desired protein. Isolated polypeptides of this invention do not contain such endogenous co-purified protein.

Protein purity or homogeneity may be indicated by a number of means well known in the art, such as polyacrylamide gel electrophoresis of a protein sample, followed by visualization upon staining. For certain purposes high resolution will be needed and HPLC or a similar means for purification utilized.

Much of the nomenclature and general laboratory procedures referred to in this application can be found in Sambrook et. al., *Molecular Cloning—A Laboratory Manual* (2nd Ed.), Vol. 1–3, Cold Spring Harbor Laboratory, Cold Spring Harbor, N.Y., 1989 or in Berger and Kimmel, *Guide to Molecular Cloning Techniques, Methods in Enzymology* 152 (Academic Press, Inc., San Diego, Calif.). The manuals are hereinafter referred to as "Sambrook" or "Berger" respectively.

Cloning

A variety of methods for cloning DNA sequences into prokaryotic cells are well known in the art. Organisms which are commonly utilized as hosts for the amplification of a vector include Escherichia, Bacillus and Streptomyces. The most common bacterial hosts are various commercially available strains of *E. coli,* due to the ease with which the organism may be cultured and the wealth of information which is available regarding the cell's life-cycle, genetics, viruses and developmental regulation. The vectors most commonly used in *E. coli* are those derived from the pBR322 plasmid and those derived from λ or M13 phage, although several vectors unrelated to any of these are also common. The Sambrook and Berger manuals contains methodology sufficient to direct persons of skill through most cloning exercises.

A number of vectors detailed in Sambrook and elsewhere may be initially cloned into *E. coli* and then subsequently transferred into a eukaryotic system without any necessity for re-cloning that part of the vector which is of interest to the person of skill. Vectors capable of replication in both prokaryotic and eukaryotic cells are generally termed "shuttle vectors" and must contain at a minimum a eukaryotic and a prokaryotic origin of replication. Several shuttle vectors are commercially available which contain polycloning sites, selectable markers for both bacterial and eukaryotic cells, promoters for both bacterial and eukaryotic expression of the gene(s) of interest, and integration sequences for insertion of the vector into the eukaryotic genome. A few examples of vectors which may be amplified in bacteria and used for transformation in eukaryotic cells include the family of P element vectors for *Drosophila melanogaster,* a number of SV40-derived vectors for the transformation of COS cells, adenovirus-derived vectors for transformation in cells containing the appropriate transcription factor for RNA polymerase III, a variety of BPV-derived vectors and the YIp5-derived vectors of *Saccharomyces cerevisiae* (see Sambrook chapter 16 and Berger chapter 53 for an overview of different vectors which may be transferred between *E. coli* and eukaryotes). General techniques for shuttling DNA between prokaryotes and eukaryotes are also described in Cashion et. al., U.S. Pat. No. 5,017,478 and Kriegler, *Gene Transfer and Expression: A Laboratory Manual,* W. H. Freeman, N.Y., (1990) which are incorporated by reference.

Expression of Recombinant Proteins

Methods for expression of recombinant proteins may be found in Sambrook chapters 16 and 17.

Recombinant proteins may be expressed in either bacteria such as *E. coli* or in eukaryotic expression systems. In general, it is often necessary to express membrane proteins in eukaryotic systems to achieve proper post-translational modification of the proteins although it is sometimes possible to engineer the biologically active fragment of a polypeptide into an appropriate bacterial expression system, or to use the bacterial system for generating peptides which may be used for antibody generation. In these prokaryotic hosts, one can make expression vectors which will typically contain expression control sequences compatible with the host cell (e.g., an origin of replication) In addition, a variety of well-known promoters or promoter elements will be present, such as the lactose promoter system, a tryptophan (trp) promoter system, a beta-lactamase promoter system, or a promoter system from phage lambda (see Yanofsky, C., 1984, *J. Bacteriol.,* 158:1018–1024 and Herskowitz, I. and Hagen, D., 1980, *Ann. Rev. Genet.,* 14:399–445). The promoters will typically control expressions optionally with an operator sequence, and have ribosome binding site sequences and similar elements for initiating and completing transcription and translation.

Methods for expressing large amounts of a protein in a bacterial cell are often invaluable in determining the protein's function, or in generating simple methods of purifying a proteins such as by raising antibodies to a protein expressed in a bacterial cell for use in an immunopurification technique for isolation of a protein from a eukaryotic cell. During purification from *E. coli,* the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration, U.S. Pat. No. 4,511,503. The most common of these techniques is the generation of fusion proteins which express a portion of the protein of interest fused to a known antigen which is not otherwise present in the bacterial cell (e.g., LacZ in *E. coli*), but for which antibodies are readily available. After purification using immunopurification methods directed against the known antigen, the fusion protein is used to raise antibodies via standard techniques.

Expression of genes in eukaryotic systems may be used for a number of purposes, including the following: to confirm the identity of a cloned gene, to express eukaryotic genes which require post-translational modifications to produce large quantities of proteins which are ordinarily available in small quantities from naturally-occurring biological sources, to study the biosynthetic pathway of the gene product, to clarify the relationship between the structure and function of a protein through mutational analysis, to properly express proteins containing introns which prokaryotes cannot process, and to identify the gene's promoter elements. When choosing an expression vector several factors need to be taken into account including the size of the gene (some packaging viruses may incorporate only relatively small amounts of DNA), the type of host cell which is available (some cells such as CHO cells add more post-translational modifications than other cells such as NIH-3T3 cells), whether a permanent transformant or a transient expression system is desired and the presence of control elements in the vector. Eukaryotic expression vectors contain both prokaryotic origins of replication (generally derived from pBR322) and eukaryotic transcription units which are transcribed only in eukaryotes. The eukaryotic transcription unit consists of non-coding sequences and sequences coding for selectable markers such as thymidine kinase, aminoglycoside phosphotransferase or dihydrofolate reductase, as well as the portion of the gene of interest necessary for expression. In general the transcription unit is assembled from well-characterized viral or eukaryotic genes.

Introduction of the recombinant vectors into eukaryotic cells may be achieved by a variety of methods known in the art, including calcium phosphate or DEAE-mediated transfection, polybrene, protoplast fusion, electroporation, liposomes and direct microinjection.

Common vectors for mammalian replication systems include the Simian virus SV40e papilloma viruses such as bovine papilloma virus (BPV) and herpes viruses such as Epstein-Barr (EBV). Each of these vectors may be used to generate cell lines which contain multiple copies of the gene of interest. Call lines with high levels of expression of the introduced gene may be selected by treating the cells with gradually increasing amounts of the toxin which the selectable marker provides resistance against. The DNA unit which is amplified under selective conditions is variable, but generally includes a substantial amount of flanking DNA, particularly in stably transfected lines in which the vector has integrated into the chromosome.

The DNA sequences will be expressed in hosts after the sequences have been operably linked to an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

Many standard purification techniques may be used to purify the gene product from the gene of interest which is expressed as described above. In the present invention which provides a direct means for antibody generation, it is possible to use an immunoprecipitation or immunochromatographic method in addition to or in conjunction with standard precipitation and chromatographic methods for purification of GPV or its cleavage products, without first generating antibodies using prokaryotic fusion proteins.

As indicated above, the vectors e.g., a plasmid, which is used to transform the host cell, preferably contains DNA sequences to initiate transcription and sequences to control the translation of the antigen gene sequence. These sequences are referred to as expression control sequences.

When the host cell is of insect or mammalian origins illustrative expression control sequences are obtained from the SV-40 promoter (*Science,* 222:524–527, 1983), the CMV I.E. Promoter (*Proc. Natl. Acad. Sci.* 81:659–6631, 1984) or the metallothionein promoter (*Nature* 296:39–42, 1982). The cloning vector containing the expression control sequences is cleaved using restriction enzymes and adjusted in size as necessary or desirable and ligated with DNA coding for the GPV polypeptide by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, *J. Virol.* 45:773–781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. Biochemical Methods in Cell Culture and Virology, Kuchler, R. J., Dowden, Hutchinson and Ross, Inc., (1977). The expressed GPV polypeptides are isolated from cells grown as suspensions or as monolayers. The latter are recovered by well known mechanical, chemical or enzymatic means.

Production of GPV Peptides by Protein Chemistry Techniques

The polypeptides of the invention can be synthetically prepared in a wide variety of ways. For instance polypeptides of relatively short size can be synthesized in solution or on a solid support in accordance with conventional techniques. Various automatic synthesizers are commercially available and can be used in accordance with known protocols. See, for example, Stewart and Young, *Solid Phase Peptide Synthesis,* 2d. ed., Pierce Chemical Co. (1984). The peptides may be used to generate antibodies using standard methods, including those methods described in this application.

Alternatively, purified and isolated GPV may be treated with proteolytic enzymes in order to produce GPV polypeptides. The GPV protein sequence may be analyzed to select proteolytic enzymes to be used to generate polypeptides containing desired regions of the GPV protein. The desired polypeptides are then purified by using standard techniques for protein and peptide purification. For a review of standard techniques see, *Methods in Enzymology,* "Guide to Protein Purification", M. Deutscher, ed. Vol. 182 (1990), pages 619–626, which is incorporated herein by reference. Peptides generated by this strategy may be used to generate antibodies using standard methods, including those described in this application.

Antibody Generation

The antibodies recognizing polypeptides of the present invention are suitable for modification using the multitude of techniques available to those skilled in the art for production and manipulation of various immunoglobulin molecules. Immunoglobulins are proteins consisting of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. For a discussion of immunoglobulin forms, see e.g., *Fundamental Immunology*, 2d Ed. W. E. Paul ed, Raven Press NY (1989), Huston et al., *Proc. Nat. Acad. Sci. USA* 85:5879–5883 (1988), Bird et al., *Science* 242:423–426 (1988), and Hunkapiller and Hood, *Nature* 323:15–16 (1986).

As used herein, "immunoglobulin," "antibody" or "antibody peptide(s)" refers to polyclonal antibodies, monoclonal antibodies, to an entire immunoglobulin or antibody or any functional fragment of an immunoglobulin molecule which binds to the target antigen. Examples of such peptides include complete antibody molecules, antibody fragments, such as Fab, F(ab')$_2$, complementarity determining regions (CDRs), $V_L$ (light chain variable region), $V_H$ (heavy chain variable region), and any combination of those or any other functional portion of an antibody peptide.

An F(ab')$_2$ fragment lacks the C-terminal portion of the heavy chain constant region, and has a molecular weight of approximately 110 kD. It retains the two antigen binding sites and the interchain disulfide bonds in the hinge region, but it does not have the effector functions of an intact IgG molecule. An F(ab')$_2$ fragment may be obtained from an IgG molecule by proteolytic digestion with pepsin at pH 3.0–3.5 using standard methods such as those described in Harlow and Lane, *Antibodies: A Laboratory Manual*, Cold Spring Harbor Pubs., N.Y. (1988).

An Fab fragment comprises a light chain and the N-terminus portion of the heavy chain to which it is linked by disulfide bonds. It has a molecular weight of approximately 50 kD and contains a single antigen binding site. Fab fragments may be obtained from F(ab')$_2$ fragments by limited reduction, or from whole antibody by digestion with papain in the presence of reducing agents. (See, Harlow and Lane, supra.)

A multitude of techniques available to those skilled in the art for production and manipulation of various immunoglobulin molecules can be readily applied to produce antibodies for use in the present invention. Antibodies which bind to GPV may be produced by a variety of means. The production of non-human monoclonal antibodies, e.g., murinea lagomorpha, equine, etc., is well known and may be accomplished by, for example, immunizing the animal with a preparation containing cells bearing GPV or isolated GPV molecules. Antibody-producing cells obtained from the immunized animals are immortalized and screened, or screened first for the production of antibody which binds to GPV and then immortalized. For a discussion of general procedures of monoclonal antibody production see Harlow and Lane, supra.

The generation of human monoclonal antibodies to a human antigen is also known in the art. Generation of such human monoclonal antibodies may be difficult with conventional techniques. Thus, it may be desirable to isolate DNA sequences which encode an anti-GPV human monoclonal antibody (or portions thereof) by screening a DNA library from human B cells according to the general protocol outlined by Huse et al., *Science* 246:1275–1281 (1989). The sequences which encode the antibody (or binding fragment) of the desired specificity are then cloned and amplified. Alternatively, one may transfer the antigen binding regions of non-human antibodies, e.g., the F(ab')$_2$ or hypervariable regions, to human constant regions (Fc) or framework regions by recombinant DNA techniques to produce substantially human molecules. Such methods are generally known in the art and are described below.

The invention also provides synthetic or recombinant immunoglobulins, including chimeric immunoglobulins, humanized antibodies or hybrid antibodies or derivatives of any of those. Chimeric immunoglobulins are typically the product of chimeric DNA, which is recombinant DNA containing genetic material from more than one eukaryotic species.

"Chimeric immunoglobulins" or "chimeric antibodies refer to those antibodies or antibody peptides wherein one portion of the peptide has an amino acid sequence that is derived from, or is homologous to, a corresponding sequence in an antibody or peptide derived from a first gene source, while the remaining segment of the chain(s) is homologous to corresponding sequences of another gene source. For example, a chimeric antibody peptide may comprise an antibody heavy chain with a murine variable region and a human constant region. The two gene sources will typically involve two species, but will occasionally involve different sources from one species.

Chimeric antibodies or peptides are typically produced using recombinant molecular and/or cellular techniques. Typically, chimeric antibodies have variable regions of both light and heavy chains that mimic the variable regions of antibodies derived from one mammalian species, while the constant portions are homologous to the sequences in antibodies derived from a seconds different mammalian species. Methods for production of such antibodies are well known and are described in, for example, U.S. Pat. No. 4,816,397, and EP publications 173,494 and 239,400, which are incorporated herein by reference.

The definition of a chimeric immunoglobulin, however, is not limited to this example. A chimeric antibody is any antibody in which either or both of the heavy or light chains are composed of combinations of sequences mimicking the sequences in antibodies of different sources, whether these sources are differing classes, differing antigen responses, or differing species of origin, and whether or not the fusion point is at the variable/constant boundary.

The term "humanized" or "human-like immunoglobulin" refers to an immunoglobulin comprising a human-like framework region and a constant region that is substantially homologous to a human immunoglobulin constant region. Hence, most parts of a human-like immunoglobulin, except possibly the CDRs are substantially homologous to corresponding parts of one or more native human immunoglobulin sequences.

"Hybrid antibody" refers to an antibody wherein each chain is separately homologous with reference to a mammalian antibody chain, but the combination represents a novel assembly so that two different antigens are recognized by the antibody. In hybrid antibodies, one heavy and light chain pair is homologous to a pair found in an antibody raised against another epitope. This results in the property of multi-functional valency, i.e., ability to bind at least two different epitopes simultaneously. Such hybrids may, of course, also be formed using chimeric chains.

Immunoglobulins may be fused to functional regions from other genes (e.g., those encoding enzymes) to produce fusion proteins (e.g., immunotoxins) having novel properties. In general, modifications of the genes may be readily accomplished by a variety of well-known techniques, such as site-directed mutagenesis (see, Gillman and Smith, *Gene*, 8:8197 (1979) and Roberts, S. et al, *Nature*, 328:731–734 (1987)).

For this invention, an immunoglobulin is specific for, or reactive with, a GPV molecule if the immunoglobulin binds GPV as measured or determined by standard antibody-antigen assays, for example, competitive binding assays, saturation assays, or standard immunoassays such as ELISA or RIA. This definition of specificity applies to single heavy and/or light chains, CDRS, fusion proteins or fragments of heavy and/or light chains, that are also specific for GPV if they bind GPV alone or if, when properly incorporated into immunoglobulin conformation with complementary variable regions and constant regions as appropriate, are then capable of binding GPV. Binding affinity is typically represented by the affinity constant ($K_a$) for equilibrium concentrations of associated and disassociated configurations, i.e., $K_a=[A-B]/[A][B]$ where [A], [B], and [A-B] are the concentrations at equilibrium of the antibody (A), antigen (B) and antigen-antibody complex (A-B), respectively. Under physiological conditions, the affinity constant of a specific immunoglobulin of the present invention is typically about $10^{-3}$ to about $10^{-12}$ liters/mole, and preferably about $10^{-10}$ liters/mole or more. One of skill will recognize, however, that binding affinity between two molecules will be influenced by a number of factors such as temperature, pH, ionic strength, and the like.

Compositions of the present invention comprise immunoglobulins which selectively bind GPV molecules on platelet cells. The immunoglobulins and pharmaceutical compositions of this invention are particularly useful for parenteral administration, i.e., subcutaneous, intramuscular, or intravenous administration A number of new drug delivery approaches are being developed, and the pharmaceutical compositions of the present invention are suitable for administration using these new methods, as well. See, Langer, *Science*, 249,1527–1533 (1990).

In one embodiment, the antibodies of the present invention can be used to target conventional drugs or other agents to platelets. By using an antibody to target a drug to cells bearing GPV, such drugs can achieve higher concentrations at sites of platelet aggregation. The immunoglobulins can be directly or indirectly coupled to the chemotherapeutic agent.

The antibodies of the present invention may also be used for diagnostic purposes, such as identifying areas of platelet aggregation. For diagnostic purposes, the antibodies may either be labeled or unlabeled. Unlabeled antibodies can be used in combination with other labeled antibodies (second antibodies) that are reactive with the antibody, such as antibodies specific for a particular immunoglobulin constant region. Alternatively, the antibodies can be directly labeled. A wide variety of labels may be employed, such as radionuclides, fluorescers, enzymes, enzyme substrates, enzyme cofactors, enzyme inhibitors, ligands (particularly haptens), etc. Numerous types of immunoassays are available and are well known to those skilled in the art.

In diagnostic applications, compositions containing the immunoglobulins or a cocktail thereof, are administered to a patient suspected of having a defect in platelet functions Alternatively, the efficacy of a particular treatment can be monitored. An amount sufficient to accomplish this is defined to be a "diagnostically effective dose." In this use, the precise amounts will depend upon the patient's state of health and the binding constants for the specific antibodies employed.

Kits can also be supplied for use with the subject antibodies. Thus, the subject antibody composition of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the chimeric antibody is employed in an assays this will usually be present in a separate vial. The second antibody is typically conjugated to a label and formulated in an analogous manner with the antibody formulations described above.

PCR

The use of PCR (Hullis et. al., U.S. Pat. No. 4,683,202 (1987)) in the field of molecular biology is well known. PCR has been adapted for many diverse purposes including cloning, sequencing, forensics, diagnostics and cladistic analysis. The technique is detailed in several general sources which provide adequate guidance to one of skill to perform the technique, including Sambrook and *PCR Protocols: A Guide to Methods and Applications* (Innis et. al. eds) Academic Press Inc. San Diego, Calif. (1990) (hereinafter "Innis").

The following PCR protocol is provided as a starting point for a person of skill, who will readily recognize that it is usually necessary to optimize reaction conditions, and that optimization is especially important when the technique yields inadequate results, or when an essentially repetitive task utilizing the technique needs to be performed. In general, a 100 µl reaction contains the following: 1 to $1\times10^7$ target molecules (generally about $1\times10^5$ to $1\times10^6$ target molecules); 1 pmol–100 pmol of each primer (generally about 20 pmol), the primer having a $T_m$ of from about 30° C. to about 70° C. (preferably greater than about 50° C.) 20 mM Tris-Hcl (pH approximately 8.3 at 20° C.); 0.2 mM–5 mM $MgCl_2$ (generally about 1.5 mM $MgCl_2$; occasionally it may be helpful to substitute some of the $MgCl_2$ with $MnCl_2$); 25 mM KCl; 0.05% Tween 20; 100 µg autoclaved gelatin or nuclease-free bovine serum albumin; 5–200 µM of each dNTP (generally about 50 µM of each dNTP), and from 0.25 to 5 units (generally about 2 units) of taq DNA polymerase. Many practitioners prefer to add an oil phase on top of the aqueous phase to prevent evaporation of the reaction mixture and to prevent the reaction components from being distributed unevenly in the reaction tube upon heating. The reaction mixture is cycled through 15–65 (usually 20–35) of the following temperature variations (generally using a commercially available thermal cycler, occasionally performed by hand with 3 temperature baths): "denaturation" at 96° C. for 0.25 mine (on the first cycle it is often better to leave the reaction mixture at 96° C. for 1–5 minutes), "primer annealing" at a temperature about 5° C. to 10° C. lower than the calculated $T_m$ for 30 seconds, "primer extension" at 72° C. for 1–3 minutes depending on the length of the target sequence to be amplified. Cycling is generally concluded with a final 72° C. extension for about 5 minutes and the reaction is stopped by chilling the reactants to about 4° C. and/or by the addition of EDTA in an amount approximately 8-fold greater than the quantity of $MgCl_2$ plus $MnCl_2$ plus any other divalent cation in the mixture.

Once the complete sequence of a gene is known, it is entirely straightforward to design PCR experiments to detect the presence of abnormalities in the structure of the gene in individual organisms. After performing PCR on the individual's DNA or cDNA using primers designed from the known GPV gene sequence, the presence of gross defects in the gene or the gene's cDNA may be ascertained by standard agarose gel electrophoresis of restriction endonuclease-digested fragments of the DNA or cDNA. If desirable, all of the structural elements of a defective gene may be determined, either by direct sequencing of the PCR product, or by subcloning the PCR product into a sequencing vector for sequencing by standard methodologies; commercially available sequencing kits from a variety of sources are available for the sequencing of either PCR-generated or cloned DNA. In the present invention, the GPV gene may be examined in patients in order to diagnose Bernard-Soulier syndrome, or in order to determine any genetic predisposition towards the Bernard-Soulier syndrome in persons which may be at risk for the disease. The ability to detect genetic diseases in utero using PCR amplification of DNA from a developing fetus is also known in the art and it will be possible to detect abnormalities in the GPV gene using standard PCR methodologies. In addition, the GPV gene is a specific marker for cells of the megakaryocytic lineage and is generally useful as a morphological marker for tracking platelet development.

Southern Analysis and Northern Analysis

Southern analysis of genomic DNA and northern analysis of RNA using a cloned probe are basic to the art of molecular biology. Sambrook provides adequate guidance to perform most commonly used Southern and northern techniques including analysis of genomic DNA, mRNA and cDNA. The present invention provides an array of probes that may be constructed from the GPV gene for use in Southern analysis. These include synthetic oligonucleotide probes generated from the sequence of any region of the GPV gene, probes generated from cleavage products of the cloned gene using random-primer or terminal phosphate labeling methods and several other methods known to persons of skill. The probes may be used for a variety of purposes including isolation of homologous genes from other species by screening genomic or expression libraries or performing PCR, the identification of restriction fragment length polymorphism and the identification of tissues which express the GPV gene using in situ or northern analysis.

Pharmaceutical Composition and Therapeutic Uses of GPV Polypeptides

The recombinant proteins of the present invention may be used to boost the level of GPV and its cleavage products in a patient which exhibits a lower than normal level of the GPV or GPVfl, or at a specific site such as a wound in a patient with normal clotting. The pharmaceutical compositions of the GPV gene are intended for parenteral, oral, topical, or local administration. For the pharmaceutical compositions which are administered parenterally (e.g. intravenously, subcutaneously, intradermally, or intramuscularly), the invention provides compositions for parenteral administration that comprise a solution of the GPV polypeptide isolated from an expression system as described above dissolved or suspended in an acceptable aqueous carrier. A variety of aqueous carriers may be used, e.g., water, buffered water, 0.4% saline, 0.3% glycine, hyaluronic acid and the like. These compositions may be sterilized by conventional, well known sterilization techniques or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. For solid compositions, conventional nontoxic solid carriers may be used which include, for example, pharmaceutical grades of mannitol, lactose, starch, magnesium stearate, sodium, saccharin, talcum, cellulose, glucose, sucrose, magnesium carbonate, and the like.

For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the GPV polypeptide(s) are preferably supplied in finely divided form along with a surfactant and propellant. The surfactant must be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

For topical administration, e.g., to a wound, the GPV polypeptides may be administered in an aqueous solution as described above, or may be applied in a salve composed of non-toxic carrying agents such as completely polymerized polyacrylamide, or long-chain esters or partial esters of fatty acids as described above. Additionally, the solution or salve may be applied to bandages in standard wound-dressings.

In therapeutic applications, GPV polypeptides are administered to a patient in an amount sufficient to affect platelet aggregation, an amount which constitutes a "therapeutically effective dose." Amounts effective for this use will depend on several factors including the particular polypeptide, the manner of administration, the weight and general state of health of the patient, the presence of other blood disorders in the patient, the presence or severity of a wound and the judgment of the prescribing physician. This will typically be between about 1 µg/kg and about 100 mg/kg, preferably about 3 mg/kg to about 15 mg/kg.

Gene Therapy

Strategies for gene therapy are reviewed in Friedmann, *Science* 2440:1275 (1989), which is incorporated herein by reference.

Delivery of the polynucleotide of interest may be accomplished in vivo by administering the therapy vector to an individual patient, typically by systemic administration (e.g., intravenous, intraperitoneal, intramuscular, subdermal, or intracranial infusion). Alternatively, the vector may be used to deliver polynucleotides to cells ex vivo such as cells explanted from an individual patient or universal donor hematopoietic stem cells, followed by reimplantation of the cells into a patient, usually after selection for cells which have incorporated the gene for the polynucleotide.

The vector may be used for gene therapy to treat congenital genetic diseases, acquired genetic diseases (e.g., cancer), viral diseases or to modify the genome of selected types of cells of a patient for any therapeutic benefit. A treatable disorder using the GPV gene of the present invention is the Bernard-Soulier syndrome. Polynucleotides which reverse or suppress the neoplastic phenotype (e.g. antisense inhibition of defective GPV expression) may be used to treat defective GPV expression as well as engineering the normal GPV gene into patients.

The following examples are offered by way of illustration, not limitation.

EXAMPLES

The following examples are offered by way of illustration and do not limit the claims. It will be apparent to one of skill that many of the experimental parameters may be altered.

Materials: The following applies to materials used in the Examples below: Restriction endonucleases, modifying enzymes, and the M13 cloning vector were purchased from Boehringer, Mannheim, Germany. The pBluescript KSII vector was obtained from Stratagenee San Diego, Calif. The Gene Clean II kit was from Bio 101, La Jolla, Calif. Radiolabeled nucleotides, Hybond $N^+$ membranes and Hyperfilm X-ray films were obtained from Amersham Corp., Les Ulis, France. Nitrocellulose membranes were from Schleicher and Schuell, Ecquevilly, France. Synthese Oligonucleotides were obtained from the Service de Synthase des oligonucleotides, INSERN U 184, LGME, Strasbourg, France or synthesized on a Beckmann Oligo 1000 oligonucleotide synthesizer (Beckmann, Gagny, France). All reagents were molecular biology grade.

Example 1 cDNA Cloning of Human Platelet Glycoprotein V via PCR Amplification of Platelet and Megakaryoctye cDNA In order to clone the cDNA encoding glycoprotein v via PCR, a series of degenerate primers were designed based on published partial peptide sequences (Shimomura, et. al., *Blood* 75:2349–2356 (1990)) obtained from purified platelet GPV. Fresh human platelets were isolated and platelet total RNA was prepared according to previously described procedures (Lanza et. al., *J. Clin. Invest.* 89:1995–2004 (1992) and Wicki et. al., *Thromb. Haemostas* 61:448–453). Megakaryocyte RNA kindly provided by Dr. Nelly Kieffer, Laboratoire Franco-Luxembourgeois de Recherche Biomedicale, Luxembourg, was from a patient suffering from megakaryoblastic leukemia. Platelet or megakaryocyte polya$^+$ RNA was used to synthesize cDNA with a commercial kit (Boehringer Mannheim). First strand synthesis was performed by priming with oligo dT or by priming with degenerate or exact primers specific for GPV and extending with 20 units of M-MLV reverse transcriptase (Gibco-BRL, Cergy Pontoise, France). Approximately 25 ng of platelet or megakaryocyte cDNA was used in the PCR amplification reaction using a Gene Amp DNA amplification reaction kit (Perkin-Elmer Cetus, St. Quentin, France), a 0.2 $\mu$M concentration of each nucleotide primer, and 1 unit of Taq polymerase. The cDNA was denatured at 94° C. for 4 min, and amplification was performed for 30 cycles with extension at 72° C. for 2 min, denaturation at 94° C. for 1 min, and primer annealing between 45 to 60° C. for 1 min depending on the primers used. Degenerate primers 1 and 4 based on peptide sequence K5/6 and running on opposite strands were used successfully to amplify a 108 bp fragment (fragment i) from oligo dT primed platelet cDNA. Sequence analysis revealed that the cDNA fragment contained within primers 1 and 4 coded for a 20 amino acid peptide corresponding exactly to the published peptide sequence (amino acid residues 13 to 33). This demonstrated that the amplified fragment corresponded to GPV cDNA. In order to obtain additional cDNA sequence, exact oligonucleotide primers were generated in the (–) strand (primer 3) and in the (+) strand (primer 2) orientation. An additional 150 bp cDNA fragment (fragment ii) was obtained using primer 3 and degenerate primer 5 based on the M6 peptide sequence. Following PCR, 10 $\mu$l of the amplification mixture was analyzed on a 1 to 2% agarose gel.

Rapid amplification of cDNA ends (RACE) was used to extend the sequence in the $_5$'- and 3'-direction (Frohman, et. al., *Proc Natl. Acad. Sci. USA.* 85:8998–9002 (1988)). Using the 31-RACE procedure two additional overlapping fragments (iii and iv) covering 703 bp of cDNA were obtained in the 3'-direction. For the 3'-RACE, 25 ng of cDNA were subjected to a first round of PCR with the Adaptor-dTI7 primer and (+) strand primer 2 or 6, followed by a second PCR with the adaptor and primer 2 (SEQ.ID.NOs. 8–9) or 6 (SEQ.ID.NO. 16) (see Table 1 for a description of the primers). The 5'-RACE procedure using (–) strand primers 7 and 8 generated two more fragments of 260 and 150 bp (v and vi) in the 5'-direction. For the 5'-RACE, cDNA was prepared from 1 $\mu$g of RNA using a (–) strand specific primer and was detailed by incubation with 5 $\mu$M DGTP and 50 units of terminal transferase (Boehringer Mannheim) at 37° C. for 10 min in the buffer supplied by the manufacturer. After phenol-chloroform extraction, the reaction mixture was dialyzed over a Centricon 30 column (Amicon, Beverly, Mass.) and used in the PCR reaction. A first round of PCR was performed with the Adaptor-dC12 primer and primers 7 or 8 followed by a second round of PCR with the adaptor alone and primers 7 or 8.

The positive fragments obtained from regular PCR or from the RACE approach were end-cleaved with restriction enzymes (usually Eco RI and Sal I), isolated by electrophoresis on Sea Plaque agarose (FMC Bioproducts, Rockland, Me.), purified using the Gene Clean II kit, and subcloned into the M13 or pBluescript vectors. The inserts were sequenced using the Sequenase kit (United States Biochemical Corp., Cleveland, Ohio) with DATP 5'α-[$^{35}$S]-thiophosphate. All the fragments obtained by the PCR approach were analyzed by sequencing on both strands and their identity to GPV was assessed by comparison to the published GPV partial sequences.

Using the strategy described above we were able to assemble 1,199 bp of GPV cDNA from 6 fragments amplified from platelet mRNA. Sequence analysis revealed the presence of 31 bp of 5' untranslated sequence followed by a 1,168 bp open reading frame starting with a methionine and coding for a total of 389 amino acids.

Example 2

Southern Analysis of Human Chromosomal DNA

In order to determine the complexity of the human GPV gene, a Southern blot analysis was performed under high stringency on human chromosomal DNA using a 748 bp cDNA probe corresponding to the coding region. High molecular weight human leukocyte DNA was digested to completion with restriction endonucleases and subjected to electrophoresis on 0.7% agarose gels. The fragments were transferred to a Hybond N+ nylon membrane and were hybridized to a 748 bp $^{32}$P-labelled GPV cDNA fragment at 45° C. overnight. The hybridization buffer was 50% (v/v) formamide, 0.9 M NaCl, 50 mM NaH$_2$PO$_4$, 2 mM EDTA, 1% (w/v) SDS, 5% (w/v) dextran sulfate, 0.02% (w/v) polyvinylpyrrolidone, 0.02% (w/v) Ficoll 400, and 50 μg/ml salmon sperm DNA. Membranes were washed in 0.5×SSC, 1% (w/v) SDS at 60° C. and autoradiographed.

Figure 4:
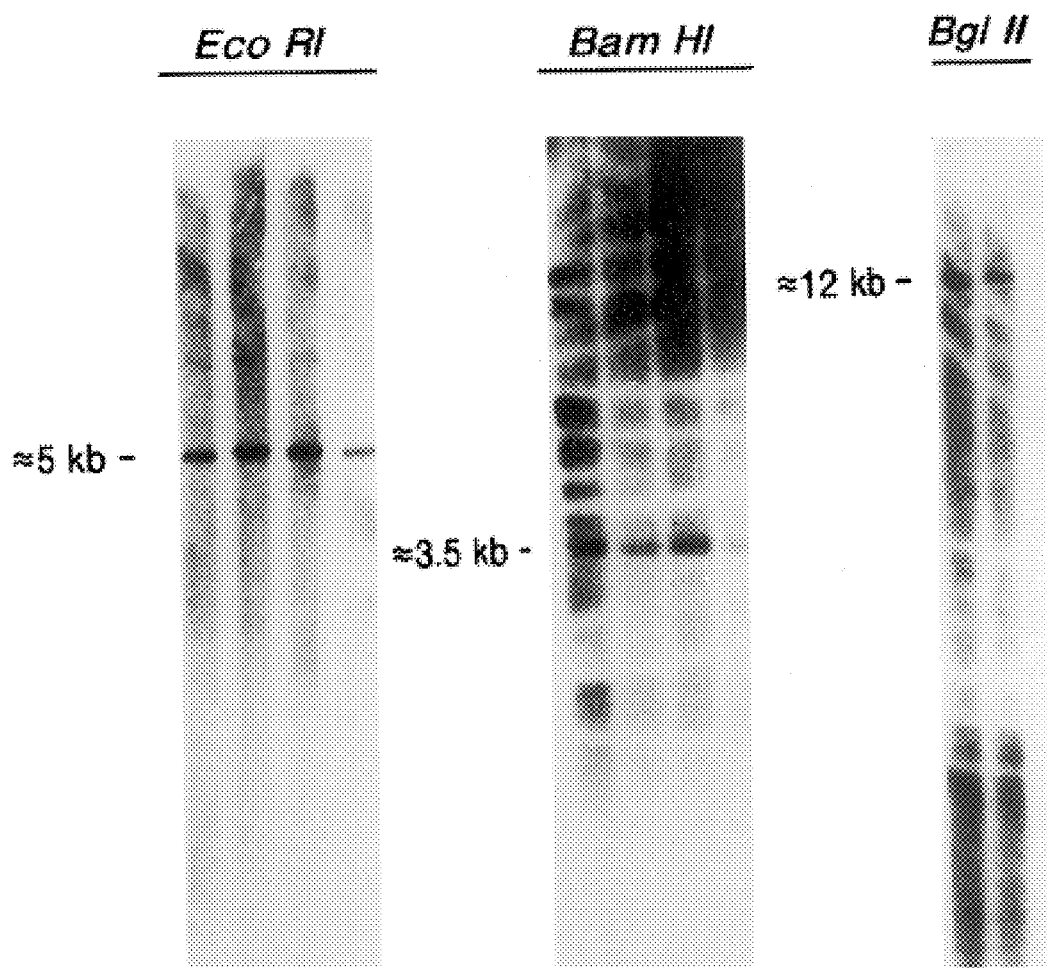
FIG. 4: Southern blot analysis. High molecular weight genomic DNA 10 vg) from human leukocytes was cut with an excess of Eco RI, Bam HI, and Bgl II restriction endonucleases, separated on a 0.7% agarose gel, and transferred to Hybond N$^+$ nylon membranes. The filters were probed with a 748 bp $^{32}$p-labelled GPV cDNA fragment. The size of the hybridizing bands in kilobase pairs was estimated by comparison with λ/Hind III DNA fragments.

Single positive bands of approximately 5 kb, 3.5 kb, and 12 kb were observed when the DNA was cut with Eco RI, Bam HI, and Bgl II restriction endonucleases, respectively (FIG. 4). Analysis of additional individuals revealed an extra polymorphic Bgl II band of 3.4 kb. This simple hybridization pattern was suggestive of a single copy gene of low complexity.

Example 3

Northern Analysis of Platelet mRNA

Figure 3:
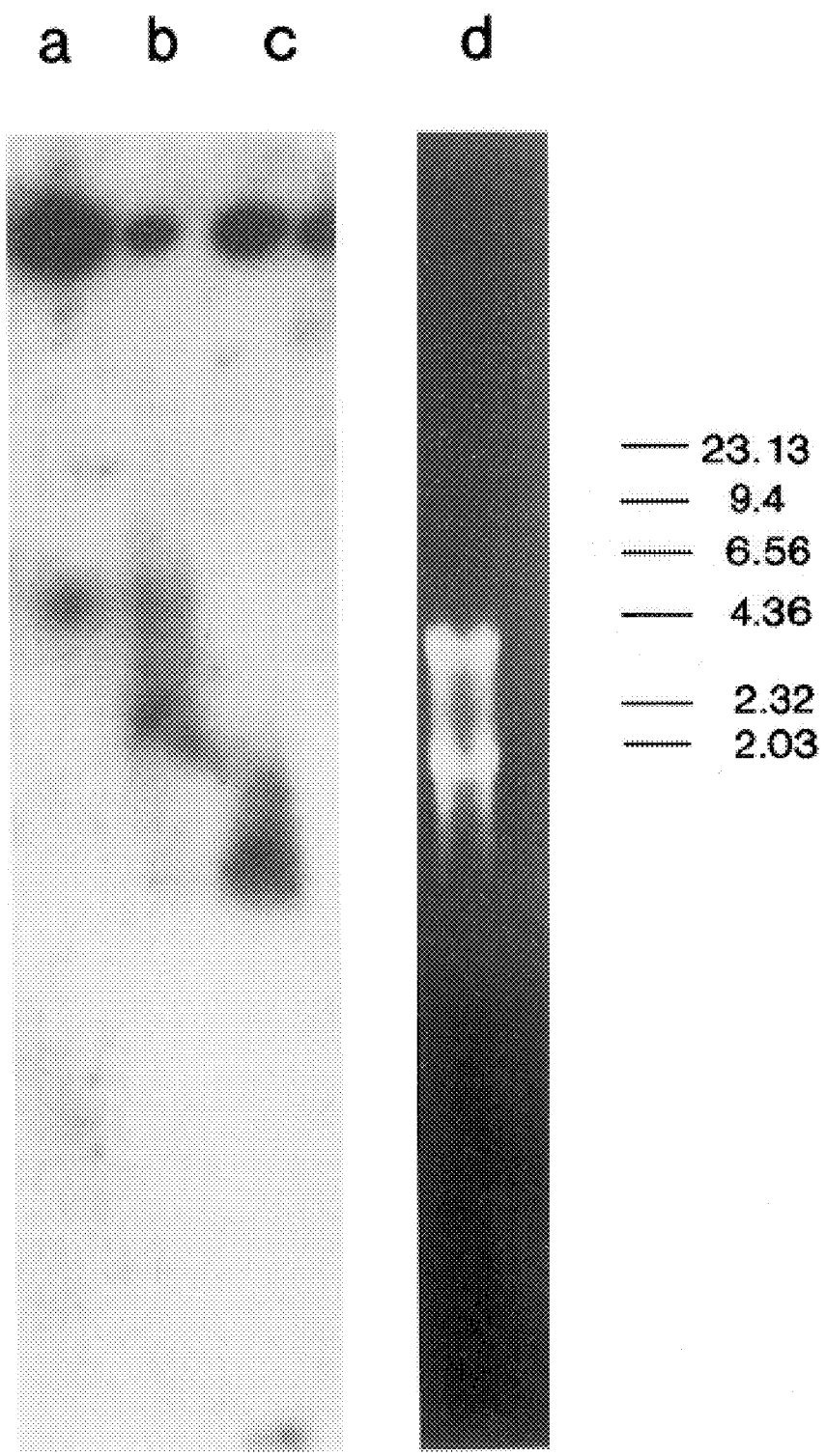
FIG. 3: Northern blot analysis. Total RNA (10 µg per lane) from human platelets (lanes a and b) and human monocytes (lane c) was electrophoretically separated on 1% agarose-formaldehyde gel, transferred to Zetaprobe, and probed with a 748 bp random prime $^{32}$P-labelled cDNA probe. Lane d is an ethidium bromide stained gel of leukocyte total RA showing the position of 28S and 18S ribosomal RNA. The molecular size was calibrated by reference to the migration of λ/Hind III DNA fragments indicated in kilo base pairs.

In order to determine the size of the platelet GPV mRNA, Northern blot analysis was performed on human total platelet RNA using a 748 bp cDNA probe corresponding to the coding region (FIG. 3). Total RNA (10 μg) from platelets (leukocyte contamination <10$^{-7}$) or monocytes was electrophoresed on 1% formaldehyde-agarose gel, and transferred to a Zetaprobe (Biorad) membrane. A 748 bp GPV cDNA probe (50 ng) was labelled with [α-$^{32}$P]-dCTP using the random prime labelling method and cleaned on a Nick column (Pharmacia) (incorporation [α-$^{32}$P]-dCTP was 71%). The hybridization conditions were 0.5 M NaH$_2$PO$_4$, pH 7.2, 1 mM EDTA, and 7% SDS at 65° C.

Analysis of the gel revealed a single transcript of approximately 4.5 kb. A partially degraded RNA revealed a more complex pattern. A transcript of less than 2 kb was also revealed with monocyte RNA.

Example 4

Isolation and Characterization of GPV Genomic Clones

With the 748 bp fragment as a probe 15 genomic clones were isolated from a human fibroblast genomic library in the phage λFix vector. Approximately 8×10$^5$ recombinants of a human commercial genomic library in the λFix vector (Stratagene) were plated on E. coli LE392, transferred to nitrocellulose membranes, and probed with a 748 bp $^{32}$p labelled GPV cDNA fragment. The hybridization conditions were 50% (v/v) formamide, 5×SSC, 0.1% (w/v) SDS, 5×Denhardt's medium, and 0.1 mg/ml salraon sperm DNA at 42° C. overnight. The filters were washed in 0.1×SSC, 0.05% (w/v) SDS at 56° C., dried and exposed for autoradiography. Positive clones were subjected to two additional rounds of screening in order to obtain isolated clones. Phage DNA was purified using the liquid lysis procedure. The DNA was digested with EcoRI, separated on a 0.7% agarose gal, transferred to nitrocellulose, and hybridized to the $^{32}$p-labelled GPV cDNA fragment to localize exon containing fragments. The positive fragments were subcloned into the pbluescript vector for further restriction enzyme analysis, and finally subcloned into the M13 sequencing vector. After characterization by restriction endonuclease mapping and Southern blot analysis, clone G5a was chosen for further subcloning, restriction enzyme analysis, and nucleotide sequencing.

A 7.5 kb portion of the G5a clone, shown in FIG. 1 with a partial restriction map, was entirely sequenced on both strands. Comparison with the cDNA sequence obtained by PCR revealed that the 7.5 kb genomic fragment contained the entire 1,198 bp cDNA sequence in two exons (FIGS. 5A–C (SEQ.ID.NO. 1)) separated by a 958 bp intron. Exon 1 contained 29 bp of 5'-untranslated region and exon 2 was composed of 2 bp of 5'-untranslated sequence and 1,168 bp of coding sequence obtained by PCR. Exon 2 contained an additional 512 bp of coding sequence before reaching a TAA stop codon.

The sequence immediately adjacent to the 5'-end of the cDNA (exon 1) was examined for the presence of cis-regulatory elements. The analysis revealed the presence of a sequence which matched the consensus sequence for a TATA box (5'-TATATA-3') characteristic of RNA polymerase II transcribed genes, but did not reveal a consensus sequence for a CAAT box. The TATA box was followed 31 bp downstream by a putative Cap site. An additional sequence (TATAT) with similarity to the TATA box consensus was found at position 1,199. A 5'-AAGATA-3' and a 5'-AGATAG-3' sequence with similarity to the consensus 5'-(AT)GATA(AG)-3' motif for a GATA-1 binding site (Faisst and Mayer Nucleic Acids Research 20:3–26 (1992)) were located at position 1,285 and 1,321 respectively. The GATA motif has been found in the promoters and enhancers of all characterized erythroid and megakaryocyte specific genes. Other motifs for cis-acting elements include Ets-1 cis-acting sequences at positions 471 (5'-CAGGAAGT-3'), 493 (5'=GAGGAAGC-3'), 897 (5'-GCATCCTG-3', inverse), 1,178 (5'-ACTTCCC-3', inverse) and, 1,365 (5'-CAGGATGCAA-3') (SEQ.ID.NO 3) (consensus sequence: 5'-(GC)(AC)GGA(AT)G(TC)), and a Sp1 putative binding site at position 1,142 (5'-GGGGTGTGGC-3') (SEQ.ID.NO. 4), (consensus sequence: 5'-(GT)(GA)GGCG(GT)(GA) (CT)-3'). A putative TPA responsive element (TRE)(5'-TGACTGACT-3') was found at position 68. Analysis of 3,348 bp of genomic sequence 3'- of the TAA termination site revealed the presence of putative polyadenylation AATATA sites at positions, 5,610, 6,966, 7,224, and 7,358. Two Alu repetitive sequences (Schmid and Jelinek Science 216:1065–1070 (1982) were located at positions 598–896, and 6,133–6,440.

Nucleotide sequence comparison and assembly was performed using the PC Gene software developed by Intelligenetics Inc., Palo Alto, Calif.

Example 5

Determination of The Primary Amino Acid Structure of GPV

The amino acid sequence of GPV as deduced from its cDNA and genomic sequences is shown in FIG. 5D (SEQ.ID.NO. 2). GPV was found to be composed of 560 amino acids, including a putative 16 amino acid signal peptide, and a putative C-terminal 25 amino acid transmembrane domain. Between the signal peptide and the transmembrane domain, is a sequence of 503 amino acids containing eight potential N-glycosylation sites (NXS, NXT) and eight cysteine residues. The putative transmembrane domain is followed by a 16 residue hydrophilic segment. The carboxy region of the transmembrane domain contains basic residues which are typically found on the cytoplasmic side of the integral membrane proteins (Sabatini et. al., *J. Cell. Biol.* 92:1–22 (1982)). These features suggest that GPV is a type I integral membrane protein with most of its polypeptide chain located outside the call (FIG. 8). The predicted molecular weight of the GPV polypeptide after removal of the signal peptide is 59,276 Da. Assuming a weight of 2,500 Da per oligosaccharide moiety, the addition of eight N-linked carbohydrates to the GPV polypeptide backbone would bring the weight to 79,276 Da, close to the reported 82 kDa apparent molecular weight estimated by SDS-PAGE analysis (Berndt and Phillips *J. Biol. Chem.* 256:59–65 (1981); Shimomura et. al., *Blood* 77:2349–2356 (1990); Zafar and Walz *Thromb. Res.* 53:31–44 (1989)).

Analysis of the GPV extracellular sequence revealed the presence of 15 leucine-rich tandem repeats of 24 amino acids (FIG. 6) (SEQ.ID.NOs. 22–36). These repeats are very similar to repeats found in platelet GPIBα, GPIBβ and GPIX, and to the 24 amino acid consensus sequence based on the repeats found in other members of the LRG family (SEQ.ID.NO. 37). The last GPV Leu-rich repeat (SEQ.ID.NO. 36) is flanked on its C-terminal side by a sequence (NSWRCDCGL) (SEQ.ID.NO. 5) similar to sequences described at the C-terminal end of Leu-rich domains in other members of the LRG family (Hickey et. al., *Proc. Natl. Acad. Sci. USA* 86:6773–6777 (1989)).

Thrombin-induced cleavage of GPV results in the generation of a soluble fragment (GPVfl) of approximately 69 kDa. At position 476–477 a sequence was found containing an RG dipeptide which represents a potential cleavage site for thrombin (Stubbs and Bode *Thromb. Res.* 69:1–58 (1993)). Proteolytic cleavage at this RG site would cause a 67,613 Da loss in the molecular weight of GPV. Comparison of the sequence flanking the RG site to sequences of other known thrombin substrates revealed significant homology to the Aα and Bβ chain of human fibrinogen, to human plasma FXIII, and to human chorionic gonatropin β-subunit (FIG. 7) (SEQ.ID.NOs. 38–43). Amino acid sequence comparison and assembly was performed using the PC Gene software developed by Intelligenetics Inc., Palo Altos Calif.

The new N-terminal sequence revealed by the potential cleavage site matched that of the Th1 peptide obtained after N-terminal sequencing of thrombin-cleaved platelet GPV (Shimomura et. al., *Blood* 75:2349–2356 (1990); Roth et. al., *Biochem. Biophys. Res. Commun.* 170:152–161 (1990)). Inspection of the sequence surrounding the RG dipeptide did not reveal a cluster of negatively charged residues which are known to be responsible for the interaction of thrombin with the newly cloned thrombin receptor (Vu et. al., *Cell* 64 1057–1068 (1991)) or like those in GPIBα, another thrombin-binding membrane glycoprotein (Lopez et. al., *Proc. Natl. Acad. Sci. USA* 85:2135–2139 (1988).

EXAMPLE 5

Figure 2A:
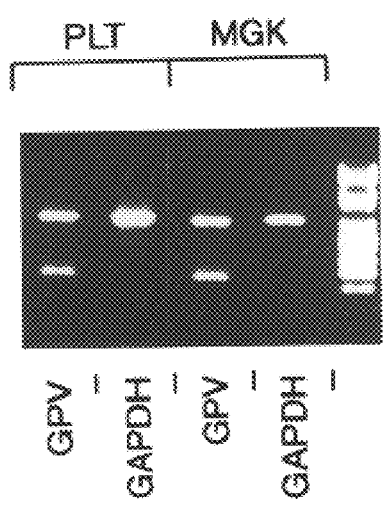
FIG. 2A illustrates the detection of GPV mRNA in platelets and megakaryocytes by RT-PCR amplification.
Figure 2B:
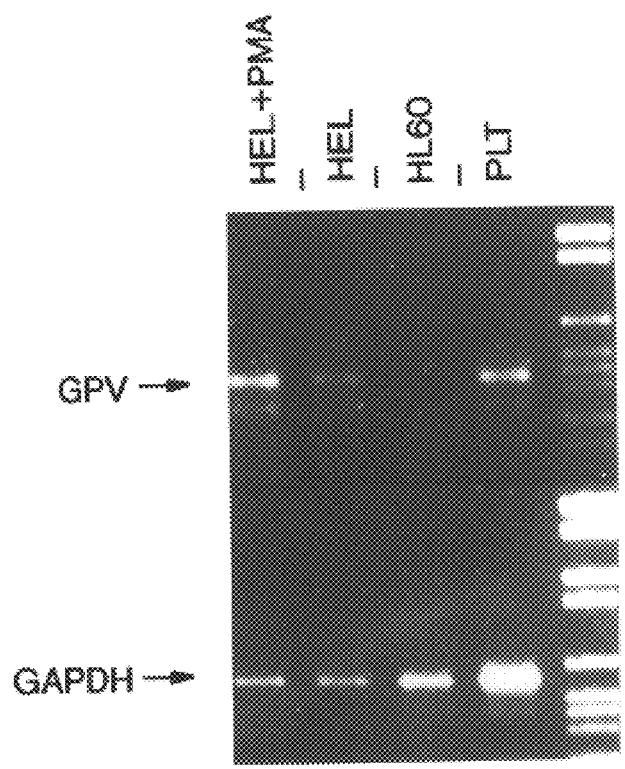
FIG. 2B illustrates the detection of GPV mRNA in HEL cells by RT-PCR amplification. Total RNA (25 ng) was subjected to reverse transcription followed by PCR with GPV cDNA based primers, and in a control reaction with primers for the housekeeping GAPDH gene. Ten µl of the PCR reactions were separated on a 2% agarose gel stained with ethidium bromide and are shown together with Bgl I/Hinf I cut pBR328 DNA molecular-weight markers.

Determination of the Cellular Distribution of Human Platelet Glycoprotein v message via RT-PCR The cellular distribution of GPV mRNA was assessed using the sensitive RT-PCR amplification technique using primers from the cDNA sequence. GPV mRNA was detected in platelets, megakaryocytes and HEL cells, and was increased in HEL cells after stimulation with phorbol ester, but was not detected in HL60 cells, K562, U937, or endothelial cells (FIG. 2).

All publications, patents, and patent applications herein are incorporated by reference to the same extent as if each individual publication, patent or patent application was specifically and individually indicated to be incorporated by reference.

Although the present invention has been described in some detail by way of illustration and example for purposes of clarity and understanding, it will be apparent that certain changes and modifications may be practiced within the scope of the appended claims.

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
        (A) LENGTH: 7452 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Homo sapiens (ix) FEATURE:
        (A) NAME/KEY: intron
        (B) LOCATION: 1462..2419

(ix) FEATURE:
        (A) NAME/KEY: CDS
        (B) LOCATION: 2422..4101

(ix) FEATURE:
        (A) NAME/KEY: misc_signal

```
       (B) LOCATION: 68..76
       (D) OTHER INFORMATION: /function= "Putitive TPA responsive
           element"
           /label= TRE (ix) FEATURE:
       (A) NAME/KEY: misc_signal
       (B) LOCATION: 471..478
       (D) OTHER INFORMATION: /function= "Ets-1 cis-acting
           sequence"
           /label= Ets-1

(ix) FEATURE:
       (A) NAME/KEY: misc_signal
       (B) LOCATION: 493..502
       (D) OTHER INFORMATION: /function= "Ets-1 cis-acting
           sequence"
           /label= Ets-1

(ix) FEATURE:
       (A) NAME/KEY: repeat_region
       (B) LOCATION: 593..881
       (D) OTHER INFORMATION: /rpt_type= "other"
           /label= Alu (ix) FEATURE:
       (A) NAME/KEY: misc_signal
       (B) LOCATION: 897..904
       (D) OTHER INFORMATION: /function= "Ets-1 cis-acting
           sequence"
           /label= Ets-1

(ix) FEATURE:
       (A) NAME/KEY: misc_binding
       (B) LOCATION: 1142..1149
       (D) OTHER INFORMATION: /function= "Sp1 binding site"
           /standard_name= "Sp1"

(ix) FEATURE:
       (A) NAME/KEY: misc_signal
       (B) LOCATION: 1178..1184
       (D) OTHER INFORMATION: /function= "Ets-1 cis-acting
           sequences"
           /label= Ets-1

(ix) FEATURE:
       (A) NAME/KEY: TATA_signal
       (B) LOCATION: 1199..1203

(ix) FEATURE:
       (A) NAME/KEY: TATA_signal
       (B) LOCATION: 1263..1269

(ix) FEATURE:
       (A) NAME/KEY: misc_binding
       (B) LOCATION: 1285..1289
       (D) OTHER INFORMATION: /function= "GATA-1 binding site"

(ix) FEATURE:
       (A) NAME/KEY: misc_binding
       (B) LOCATION: 1321..1326
       (D) OTHER INFORMATION: /function= "GATA-1 binding site"

(ix) FEATURE:
       (A) NAME/KEY: misc_signal
       (B) LOCATION: 1365..1372
       (D) OTHER INFORMATION: /function= "Ets-1 cis-acting
           sequences"
           /label= Ets-1

(ix) FEATURE:
       (A) NAME/KEY: repeat_region
       (B) LOCATION: 6133..6440
       (D) OTHER INFORMATION: /rpt_type= "other"
           /label= Alu (ix) FEATURE:
       (A) NAME/KEY: misc_signal
       (B) LOCATION: 5610..5615
```

(D) OTHER INFORMATION: /standard_name= "Polyadenylation
                signal sequence"

(ix) FEATURE:
            (A) NAME/KEY: misc_signal
            (B) LOCATION: 6966..6971
            (D) OTHER INFORMATION: /standard_name= "Polyadenylation
                signal sequence"

(ix) FEATURE:
            (A) NAME/KEY: misc_signal
            (B) LOCATION: 7224..7229
            (D) OTHER INFORMATION: /standard_name= "Polyadenylation
                signal sequence"

(ix) FEATURE:
            (A) NAME/KEY: misc_signal
            (B) LOCATION: 7358..7363
            (D) OTHER INFORMATION: /standard_name= "Polyadenylation
                signal sequence"

(ix) FEATURE:
            (A) NAME/KEY: misc_feature
            (B) LOCATION: 1..7452
            (D) OTHER INFORMATION: /standard_name= "Nucleotide
                sequence containing the human GPV gene"

(xi) SEQUENCE DESCRIPTION: SEQ ID NO:1:

```
TGATCGGAAC TGAAAGACCT CCCGCGATAC CTGGCAGAGG CAGTGGCTCT TCCCTGTGGT      60

CCAGGGCTGA CTGACTTTGA AGGTAATTTC AGTCAACCCA GCCTTTACTG GGCTCTGACT     120

GCATTAGGCT GCATCAAAGG GGATTGGATC CCATGATTCT TTATATCTTC TGACATTAAG     180

CCTTTGTCAG CTATAGGTGT TACAAATATC TTTAGTTTGT GGTTTATCTT TTCCCCTTTT     240

TTATGGTGTC TTGAAGGATA GAAGTCTTAA TGCAGACAGC ATTATCAGTG TGTTCAAAAG     300

ACAGCTAGAC ACGTTTTGCC TATAGACAAA TGGGCAAAAG GAAACCCAGC TTTCTCAAAT     360

GAAGCACAAG TGGGCCTTAA TTATGTGAAA AGGTGTTCAA GTTCATCATT AAACAGGGAA     420

AGGAAAAGTT AAAACCATGC TGAGATATCT TTCATAGAAA TGGCAAAAAG CAGGAAGTGC     480

CACGTGTGGG CAGAGAGGAA GCACAGGAAC TCTCACAAAT GGCAGGTGTC ATCGTAGACC     540

AACACAACCA CTTTGGAGAG CAGTTTGACT TTCCCCAGTT AAACTGAACA TGTGAGCGGC     600

CGGGCGTGGT GGCTCATGCC TGTAATCCCA GCAGTTTGGG AGGCCGAGGC GGGCGGATTG     660

CCTGAGCTCA GGAGTTCAAG ACCAGCCAGG GCAACACGGT AAAACCCCGT CTCTACTAAA     720

ATACAAAAAA TTAGCTGGGC GTGATGGTGT GTGCCTGTAA TCCCAGCTAC TTGTGAGGCC     780

GAGGCAGGAG AATTGCTTGA ACCAGGGAGC AGGAGGTTGC AGTGAGCCGA GATCGCACCA     840

CTGCACCCCA GCCTGGCGAC AGAGTCCCCC TCCCCCACCA AAAAACAAC AAGTGAGCAT      900

CCTGCAACCT AGCAATGCCA TTGTTGAACA AGTTCAAAGA TGTTCTTAGC CTTATTAGTC     960

CCAAAAGGAA GAAAAAAATG GAGGATTTGA GAATGTTCTT AGCTTTATTG CTAAGCGGAG    1020

AAAGAAAAAC AACACATACC AAAAAAAAAA AAAAAAAAAA AAAAAAACAA AAACCTGGG     1080

TGGGAAATTA GGGCCATGTG GCATGAAAAG GAAGACCCAG GGGAAGTGTG GCCCATCTAG    1140

GGGTGTGGCT ACTGCAGTGA TCCAGCTGTA TCACTGAACT TCCCTGGCAT CATAGAGTTA    1200

TATTGTGCCA TTTATGGAAA AACTCTCCCC ACTGCTCTTG GCTTTGACAG TAGGAATCAG    1260

GTTATATATG GTCTCTCGGT TTGAAGATAT TTGTCATTAA AAACCAGAAC AAGGGCTCTG    1320

AGATAGGGTC CTTTCCTGAC CTACTCTGGT AAAGTCTTTA TCCTCAGGAT GCAAGGATAC    1380

CACCCTCTTC CTGTGGAAAG TGTCGAATCA CATGCAGAGC TCTAAGTCTT TCAGTTACTT    1440

TGGAGTGCAG AACCATTTCA GGTAAGGCCA AATATTTTAA ACATTAGTAT AGGAAATTAG    1500
```

-continued

```
AGGGCTCTTT AGTCTGTGTG TGCATGAGAA GTAAAATTGC ACGAGAAGCA ATTTATGTAA      1560

AATTTCGCTT AGGAAACATT GTTTTGGCAG GTTAGTAGTA TGGTGTGCAT TTCCCAGAAA      1620

ATTCAGTGCC GTGAGTATTA CCTTTAGTTA AGCATCTTAG AAATAGTAGC TCTTATTGTT      1680

TATGGCTAAG TCAGAAATAC TACCCTCAAA TTCTATGTGA CCCTAGTTAT ACTGTTGAGC      1740

CTTTCTGTGC CTCTGTGCCT TCATCCTTGA ATCGGGGATA ATATACTTAC CTCCTAAGGT      1800

TATTGTAAGG ATTAAATGCA TGTAGTATAA ATAAAGAGCT GAGAACAATG CATGGCGTAA      1860

AGTGATAGGT ATTATTATAT GCTTTTGTTG GCTGTTGATT GAAGGTGTTC GCTGTTTTGG      1920

GGGTGTCCTT TAATAGAGTA ACTTGGTACT GTGGAAATAG CATGATTGTG AGCAAAAGAA      1980

TCAGATGGTG GTGGCTGCAG ACTTTGCTGT TCCCTTCTTG ACTGTTGGTT ATAGCCAATG      2040

CAGGGTAAGT TATAAAGTCA AGAGCAGAGC CGTTTTCACA ATGGACATTG CTTTGTGATG      2100

TCTGTGAGCT TGAATGTGAG AATGATTATT TTAATTCTCT ATGTAAAGAC TTTAAAGTAT      2160

TGGCTATTCG GTAGCTTGAT TTCTCTGTAA TCTCATGCTT TAAACTGAGA GTGGAAAATC      2220

AATAAAGCAA AAGCATGAGG CCACGCAGTG TAGAATGAGT GTCTTTTCAC CACGTAGGGA      2280

AATCTGTAGT CCTAAGAAAA GAGGGAGTGA GAATTCTGGC GAAAAGATTG TGCCTCTGCA      2340

CAAAGTGCAG GATCCCAGGG TTCAGTACAG GCGCGAACGC TCCTGTGTGT TGACCACACT      2400

CCCACGGTTG CTTTTTCAGA C ATG CTG AGG GGG ACT CTA CTG TGC GCG GTG        2451
                         Met Leu Arg Gly Thr Leu Leu Cys Ala Val
                           1               5                  10

CTC GGG CTT CTG CGC GCC CAG CCC TTC CCC TGT CCG CCA GCT TGC AAG        2499
Leu Gly Leu Leu Arg Ala Gln Pro Phe Pro Cys Pro Pro Ala Cys Lys
            15                  20                  25

TGT GTC TTC CGG GAC GCC GCG CAG TGC TCG GGG GGC GAC GTG GCG CGC        2547
Cys Val Phe Arg Asp Ala Ala Gln Cys Ser Gly Gly Asp Val Ala Arg
        30                  35                  40

ATC TCC GCG CTG GGC CTG CCC ACC AAC CTC ACG CAC ATC CTG CTC TTC        2595
Ile Ser Ala Leu Gly Leu Pro Thr Asn Leu Thr His Ile Leu Leu Phe
    45                  50                  55

GGA ATG GGC CGC GGC GTC CTG CAG AGC CAG AGC TTC AGC GGC ATG ACC        2643
Gly Met Gly Arg Gly Val Leu Gln Ser Gln Ser Phe Ser Gly Met Thr
60                  65                  70

GTC CTG CAG CGC CTC ATG ATC TCC GAC AGC CAC ATT TCC GCC GTT GCC        2691
Val Leu Gln Arg Leu Met Ile Ser Asp Ser His Ile Ser Ala Val Ala
75                  80                  85                  90

CCC GGC ACC TTC AGT GAC CTG ATA AAA CTG AAA ACC CTG AGG CTG TCG        2739
Pro Gly Thr Phe Ser Asp Leu Ile Lys Leu Lys Thr Leu Arg Leu Ser
                95                  100                 105

CGC AAC AAA ATC ACG CAT CTT CCA GGT GCG CTG CTG GAT AAG ATG GTG        2787
Arg Asn Lys Ile Thr His Leu Pro Gly Ala Leu Leu Asp Lys Met Val
            110                 115                 120

CTC CTG GAG CAG TTG TTT TTG GAC CAC AAT GCG CTA AGG GGC ATT GAC        2835
Leu Leu Glu Gln Leu Phe Leu Asp His Asn Ala Leu Arg Gly Ile Asp
        125                 130                 135

CAA AAC ATG TTT CAG AAA CTG GTT AAC CTG CAG GAG CTC GCT CTG AAC        2883
Gln Asn Met Phe Gln Lys Leu Val Asn Leu Gln Glu Leu Ala Leu Asn
    140                 145                 150

CAG AAT CAG CTC GAT TTC CTT CCT GCC AGT CTC TTC ACG AAT CTG GAG        2931
Gln Asn Gln Leu Asp Phe Leu Pro Ala Ser Leu Phe Thr Asn Leu Glu
155                 160                 165                 170

AAC CTG AAG TTG TTG GAT TTA TCG GGA AAC AAC CTG ACC CAC CTG CCC        2979
Asn Leu Lys Leu Leu Asp Leu Ser Gly Asn Asn Leu Thr His Leu Pro
                175                 180                 185

AAG GGG TTG CTT GGA GCA CAG GCT AAG CTC GAG AGA CTT CTG CTC CAC        3027
```

-continued

```
                Lys Gly Leu Leu Gly Ala Gln Ala Lys Leu Glu Arg Leu Leu Leu His
                            190                 195                 200

TCG AAC CGC CTT GTG TCT CTG GAT TCG GGG CTG TTG AAC AGC CTG GGC              3075
Ser Asn Arg Leu Val Ser Leu Asp Ser Gly Leu Leu Asn Ser Leu Gly
            205                 210                 215

GCC CTG ACG GAG CTG CAG TTC CAC CGA AAT CAC ATC CGT TCC ATC GCA              3123
Ala Leu Thr Glu Leu Gln Phe His Arg Asn His Ile Arg Ser Ile Ala
        220                 225                 230

CCC GGG GCC TTC GAC CGG CTC CCA AAC CTC AGT TCT TTG ACG CTT TCG              3171
Pro Gly Ala Phe Asp Arg Leu Pro Asn Leu Ser Ser Leu Thr Leu Ser
235                 240                 245                 250

AGA AAC CAC CTT GCG TTT CTC CCC TCT GCG CTC TTT CTT CAT TCG CAC              3219
Arg Asn His Leu Ala Phe Leu Pro Ser Ala Leu Phe Leu His Ser His
                255                 260                 265

AAT CTG ACT CTG TTG ACT CTG TTC GAG AAC CCG CTG GCA GAG CTC CCG              3267
Asn Leu Thr Leu Leu Thr Leu Phe Glu Asn Pro Leu Ala Glu Leu Pro
            270                 275                 280

GGG GTG CTC TTC GGG GAG ATG GGG GGC CTG CAG GAG CTG TGG CTG AAC              3315
Gly Val Leu Phe Gly Glu Met Gly Gly Leu Gln Glu Leu Trp Leu Asn
        285                 290                 295

CGC ACC CAG CTG CGC ACC CTG CCC GCC GCC GCC TTC CGC AAC CTG AGC              3363
Arg Thr Gln Leu Arg Thr Leu Pro Ala Ala Ala Phe Arg Asn Leu Ser
    300                 305                 310

CGC CTG CGG TAC TTA GGG GTG ACT CTG AGC CCG CGG CTG AGC GCG CTT              3411
Arg Leu Arg Tyr Leu Gly Val Thr Leu Ser Pro Arg Leu Ser Ala Leu
315                 320                 325                 330

CCG CAG GGC GCC TTC CAG GGC CTT GGC GAG CTC CAG GTG CTC GCC CTG              3459
Pro Gln Gly Ala Phe Gln Gly Leu Gly Glu Leu Gln Val Leu Ala Leu
                335                 340                 345

CAC TCC AAC GGC CTG ACC GCC CTC CCC GAC GGC TTG CTG CGC GGC CTC              3507
His Ser Asn Gly Leu Thr Ala Leu Pro Asp Gly Leu Leu Arg Gly Leu
            350                 355                 360

GGC AAG CTG CGC CAG GTG TCC CTG CGC CGC AAC AGG CTG CGC GCC CTG              3555
Gly Lys Leu Arg Gln Val Ser Leu Arg Arg Asn Arg Leu Arg Ala Leu
        365                 370                 375

CCC CGT GCC CTC TTC CGC AAT CTC AGC AGC CTG GAG AGC GTC CAG CTC              3603
Pro Arg Ala Leu Phe Arg Asn Leu Ser Ser Leu Glu Ser Val Gln Leu
    380                 385                 390

GAC CAC AAC CAG CTG GAG ACC CTG CCT GGC GAC GTG TTT GGG GCT CTG              3651
Asp His Asn Gln Leu Glu Thr Leu Pro Gly Asp Val Phe Gly Ala Leu
395                 400                 405                 410

CCC CGG CTG ACG GAG GTC CTG TTG GGG CAC AAC TCC TGG CGC TGC GAC              3699
Pro Arg Leu Thr Glu Val Leu Leu Gly His Asn Ser Trp Arg Cys Asp
                415                 420                 425

TGT GGC CTG GGG CCC TTC CTG GGG TGG CTG CGG CAG CAC CTA GGC CTC              3747
Cys Gly Leu Gly Pro Phe Leu Gly Trp Leu Arg Gln His Leu Gly Leu
            430                 435                 440

GTG GGC GGG GAA GAG CCC CCA CGG TGC GCA GGC CCT GGG GCG CAC GCC              3795
Val Gly Gly Glu Glu Pro Pro Arg Cys Ala Gly Pro Gly Ala His Ala
        445                 450                 455

GGC CTG CCG CTC TGG GCC CTG CCG GGG GGT GAC GCG GAG TGC CCG GGC              3843
Gly Leu Pro Leu Trp Ala Leu Pro Gly Gly Asp Ala Glu Cys Pro Gly
    460                 465                 470

CCC CGG GGC CCG CCT CCC CGC CCC GCT GCG GAC AGC TCC TCG GAA GCC              3891
Pro Arg Gly Pro Pro Pro Arg Pro Ala Ala Asp Ser Ser Ser Glu Ala
475                 480                 485                 490

CCT GTC CAC CCA GCC TTG GCT CCC AAC AGC TCA GAA CCC TGG GTG TGG              3939
Pro Val His Pro Ala Leu Ala Pro Asn Ser Ser Glu Pro Trp Val Trp
                495                 500                 505
```

| | |
|---|---|
| GCC CAG CCG GTG ACC ACG GGC AAA GGT CAA GAT CAT AGT CCG TTC TGG<br>Ala Gln Pro Val Thr Thr Gly Lys Gly Gln Asp His Ser Pro Phe Trp<br>510               515                  520 | 3987 |
| GGG TTT TAT TTT CTG CTT TTA GCT GTT CAG GCC ATG ATC ACC GTG ATC<br>Gly Phe Tyr Phe Leu Leu Leu Ala Val Gln Ala Met Ile Thr Val Ile<br>525               530                  535 | 4035 |
| ATC GTG TTT GCT ATG ATT AAA ATT GGC CAA CTC TTT CGA AAA TTA ATC<br>Ile Val Phe Ala Met Ile Lys Ile Gly Gln Leu Phe Arg Lys Leu Ile<br>540               545                  550 | 4083 |
| AGA GAG AGA GCC CTT GGG TAAACCAATG GGAAAATCTT CTAATTACTT<br>Arg Glu Arg Ala Leu Gly<br>555             560 | 4131 |
| AGAACCTGAC CAGATGTGGC TCGGAGGGGA ATCCAGACCC GCTGCTGTCT TGCTCTCCCT | 4191 |
| CCCCTCCCCA CTCCTCCTCT CTTCTTCCTC TTCTCTCTCA CTGCCACGCC TTCCTTTCCC | 4251 |
| TCCTCCTCCC CCTCTCCGCT CTGTGCTCTT CATTCTCACG GGCCCGCAAC CCCTCCTCTC | 4311 |
| TCTGTCCCCG CCCGTCTCTG GAAACTGAGC TTGACGTTTG TAAACTGTGG TTGCCTGCCT | 4371 |
| TCCCAGCTCC ACGCGGTGTG CGCTGACACT GCCGGGGGGC TGGACTGTGT TGGACCCATC | 4431 |
| CTTGCCCCGC TGTGCCTGGC TTGGCCTCTG GTGGAGAGAG GGACCTCTTC AGTGTCTACT | 4491 |
| GAGTAAGGGG ACAGCTCCAG GCCGGGGCTG TCTCCTGCAC AGAGTAAGCC GGTAAATGTT | 4551 |
| TGTGAAATCA ATGCGTGGAT AAAGGAACAC ATGCCATCCA AGTGATGATG GCTTTTCCTG | 4611 |
| GAGGGAAAGG ATAGGCTGTT GCTCTATCTA ATTTTTTGTT TTTGTTTTTG GACAGTCTAG | 4671 |
| CTCTGTGGCC CAGGCTGGCG TGCAGTGGGC CGTCTCAGTT CACTGCAGCC TCCGCCCTCC | 4731 |
| AGGTTCAAGT GATTCTCATG CCTCAGCGTT CTGAGTAGCT GGGATTAGAG GCGTGTGCCA | 4791 |
| CTACACCCGG CTAATTTTTG TACTTTTTAA AGTAGAGACG GGCTTTGCCA TATTGGCCTG | 4851 |
| GCTGATCTCA AACTCCTGGT CTTGAACTCC TGGCCACAAG TGATCTGCCC GCCTTAGCCT | 4911 |
| CCCAAAGTGC TGGGATTACA GGCGCAAGCC ACTACACCTG CCCTCTTCAT CGAATTTTAT | 4971 |
| TTGAGAAGTA GAGCTCTTGC CATTTTTTCC CTTGCTCCAT TTTTCTCACT TTATGTCTCT | 5031 |
| CTGACCTATG GGCTACTTGG GAGAGCACTG GACTCCATTC ATGCATGAGC ATTTTCAGGA | 5091 |
| TAAGCGACTT CTGTGAGGCT GAGAGAGGAA GAAAACACGG AGCCTTCCCT CCAGGTGCCC | 5151 |
| AGTGTAGGTC CAGCGTGTTT CCTGAGCCTC CTGTGAGTTT CCACTTGCTT TACATCCATG | 5211 |
| CAACATGTCA TTTTGAAACT GGATTGATTT GCATTTCCTG GAACTCTGCC ACCTCATTTC | 5271 |
| ACAAGCATTT ATGGAGCAGT TAACATGTGA CTGGTATTCA TGAATATAAT GATAAGCTTG | 5331 |
| ATTCTAGTTC AGCTGCTGTC ACAGTCTCAT TTGTTCTTCC AACTGAAAGC CGTAAAACCT | 5391 |
| TTGTTGCTTT AATTGAATGT CTGTGCTTAT GAGAGGCAGT GGTTAAAACA TTTTCTGGCG | 5451 |
| AGTTGACAAC TGTGGGTTCA AATCCCAGCT CTACCACTTA CTAACTGCAT GGGACTTTGG | 5511 |
| GTAAGACACC TGCTTACATT CTCTAAGCCT TGGTTTCCTG AACCTAAAA CAGGATAACA | 5571 |
| TAGTACCTGC TTCATAGAGT TTTGTGAGAA TTAAAGGCAA TAAAGCATAT AATGACTTAG | 5631 |
| CCCAGCGGCC TGCAGACAAT ACATGTTAAT GAATGTTAGC TATTATTACT AAAGATGAGC | 5691 |
| AATTATTATT GGCATCATGA TTTCTAAAGA AGAGCTTTGA GTTGGTATTT TTCTCTGTGT | 5751 |
| ATAAGGGTAA GTCCGAACTT TCTCATACTG GAGGTTACAT TCACATCAGT CTGTCTTCCC | 5811 |
| CTGCGGATGG CCTCAGCCCT GGGTGGCCAG GCTCTGTGCT CACAGTCCAG AGCAATGGAT | 5871 |
| CCTCCAACAC CACCAGGTGG ATGTGGAGCA GGAGAGCTGG ATCGTGGCAT TGTTTCTGG | 5931 |
| GTTCTGCAGT TGGGAGTTGG TTTCTGGGTT CTCCATTGGT CTACTTGTCT AGTCCCATAC | 5991 |
| CAGACTCACG GTCTCCATTA TTGGAGCTTT AATAATTTTT GGTATAGGGT CATCTCTCCA | 6051 |

-continued

```
CCTTGTTTTT CTTCTATTCT TGGTTCTTTG CAATTCTATG AATATTTCAG GGTCAGCATG      6111

TCAACTCCAT TGAAAACCC TGCTGGGATT TTAATAGAAC TTACAGCTCA CGCCTGTAAT       6171

CCCAGCACTT TGGGAGGCTG AGGTGGGTGG ATCACAGGTC AGGAGTTTGA GAACAGCTGG      6231

CCAAGATGGT GAAACCCCGT CTCTACTAAA AATACAAAAA TTAGCTGGGT GCGGTGGCAG      6291

GTGCCTGTAG TCCCAGCTAC TTGGGACACC GAGGCAGGAG AATCACTTGA ACCCGGGAGG     6351

CGGAGGTTGC AGTGAGCCGA GATCGTGCCA CTGCACTCTA GCCTGGGCGA CAGAGCGAGA     6411

CTCCATCTCA AAAAAAAGA AAAAGAAAAT TGCAGTAAAT TTAAAACTAA TTTGGGGAAG       6471

AATCTGTATT TTTACAATAC CTAGTGTTCT TGCCAGTAAG CATGGTTCAT CTTCCCATTT      6531

ATTTACGTCA TTTTAAATCT TTCAGTGATG TTTTAGAATT TTTTTTATAA AAACCTTCAC      6591

TATAAGAACA GAAACCAAA CACCGCATGT TCTCACTCAT AGGTGGGAAT TGAACAATGA       6651

GAACACTTGG ACACAGGGCG GGAACGTCA CACGCCTGGA CTGTTGGGGG GGTGGCTGGG       6711

AGAGGGATAG TGTTAGGAGA ATACCTAAT GTAAATGACG AGTTAATGGT GCAGCCAACC       6771

AACCTGGCAC ATGTATTCAT ATGTAACAAA CCTGCACGTT GTGCACATGT ACCCTAGAAC     6831

TTAAAGTATA TTAAAAAAAG AAACCTTGGC ACTGATTTTG TTAGATTTAT TCCTAGGTAT      6891

CCTTCCTCTT TTTTGATTTG TCATTGCTAT TGTAGATGGC ATCTTTTTAA AAAGTTATAT     6951

TTTCTAAAGC AAAAAATAAA AAAAGTTGTA TTTCTAATTT TTATTACCAA TATATAAGAA     7011

TGTAATTTAT TTTTACATAA TTATCTTATG TCTAGTAATA ATTCTGATAA TTTGCTTCTT    7071

CCTATTAAAA CCTTACACCC ATTATTGATT TATTTTTCTG TTTTAAAATA TCTTCCTGCA     7131

CTGGCTAAAA CCTCCACTAT AATGTTGAGC AGAACAGTGA GGCATCCTTA GAACTATCTT    7191

GGTTGCAAAG GGTAGGTCTC TAATGTTTCA TCAATAAATG TGATGTTTCT AGTCTGAGTT    7251

TGCTAAGTAT ATTTTAAAAT AATCAGTAAA GTTAGATTTT ATCCATTTTT ATCTTAACTA    7311

TTGAGATGCT CATATCATTT TTCTTCTTCA ATGTGTTAAA ATGGTGAATA AATTTATAGA    7371

TTTTGGAAAA GTAAATTCAT TCTTGCATTC CCGAAGTAAA CCAAGCCATG CTATGTGTAT    7431

TTAAAATATA TTGCTGAATT C                                               7452
```

(2) INFORMATION FOR SEQ ID NO:2:

(i) SEQUENCE CHARACTERISTICS:
        (A) LENGTH: 560 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Arg Gly Thr Leu Leu Cys Ala Val Leu Gly Leu Leu Arg Ala
 1               5                  10                  15

Gln Pro Phe Pro Cys Pro Pro Ala Cys Lys Cys Val Phe Arg Asp Ala
                20                  25                  30

Ala Gln Cys Ser Gly Gly Asp Val Ala Arg Ile Ser Ala Leu Gly Leu
         35                  40                  45

Pro Thr Asn Leu Thr His Ile Leu Leu Phe Gly Met Gly Arg Gly Val
     50                  55                  60

Leu Gln Ser Gln Ser Phe Ser Gly Met Thr Val Leu Gln Arg Leu Met
 65                  70                  75                  80

Ile Ser Asp Ser His Ile Ser Ala Val Ala Pro Gly Thr Phe Ser Asp
                 85                  90                  95
```

-continued

```
Leu Ile Lys Leu Lys Thr Leu Arg Leu Ser Arg Asn Lys Ile Thr His
            100                 105                 110

Leu Pro Gly Ala Leu Leu Asp Lys Met Val Leu Glu Gln Leu Phe
            115                 120                 125

Leu Asp His Asn Ala Leu Arg Gly Ile Asp Gln Asn Met Phe Gln Lys
130                 135                 140

Leu Val Asn Leu Gln Glu Leu Ala Leu Asn Gln Asn Gln Leu Asp Phe
145                 150                 155                 160

Leu Pro Ala Ser Leu Phe Thr Asn Leu Glu Asn Leu Lys Leu Leu Asp
                165                 170                 175

Leu Ser Gly Asn Asn Leu Thr His Leu Pro Lys Gly Leu Leu Gly Ala
            180                 185                 190

Gln Ala Lys Leu Glu Arg Leu Leu Leu His Ser Asn Arg Leu Val Ser
            195                 200                 205

Leu Asp Ser Gly Leu Leu Asn Ser Leu Gly Ala Leu Thr Glu Leu Gln
            210                 215                 220

Phe His Arg Asn His Ile Arg Ser Ile Ala Pro Gly Ala Phe Asp Arg
225                 230                 235                 240

Leu Pro Asn Leu Ser Ser Leu Thr Leu Ser Arg Asn His Leu Ala Phe
                245                 250                 255

Leu Pro Ser Ala Leu Phe Leu His Ser His Asn Leu Thr Leu Leu Thr
            260                 265                 270

Leu Phe Glu Asn Pro Leu Ala Glu Leu Pro Gly Val Leu Phe Gly Glu
            275                 280                 285

Met Gly Gly Leu Gln Glu Leu Trp Leu Asn Arg Thr Gln Leu Arg Thr
290                 295                 300

Leu Pro Ala Ala Ala Phe Arg Asn Leu Ser Arg Leu Arg Tyr Leu Gly
305                 310                 315                 320

Val Thr Leu Ser Pro Arg Leu Ser Ala Leu Pro Gln Gly Ala Phe Gln
                325                 330                 335

Gly Leu Gly Glu Leu Gln Val Leu Ala Leu His Ser Asn Gly Leu Thr
            340                 345                 350

Ala Leu Pro Asp Gly Leu Leu Arg Gly Leu Gly Lys Leu Arg Gln Val
            355                 360                 365

Ser Leu Arg Arg Asn Arg Leu Arg Ala Leu Pro Arg Ala Leu Phe Arg
            370                 375                 380

Asn Leu Ser Ser Leu Glu Ser Val Gln Leu Asp His Asn Gln Leu Glu
385                 390                 395                 400

Thr Leu Pro Gly Asp Val Phe Gly Ala Leu Pro Arg Leu Thr Glu Val
                405                 410                 415

Leu Leu Gly His Asn Ser Trp Arg Cys Asp Cys Gly Leu Gly Pro Phe
            420                 425                 430

Leu Gly Trp Leu Arg Gln His Leu Gly Leu Val Gly Gly Glu Glu Pro
            435                 440                 445

Pro Arg Cys Ala Gly Pro Gly Ala His Ala Gly Leu Pro Leu Trp Ala
            450                 455                 460

Leu Pro Gly Gly Asp Ala Glu Cys Pro Gly Pro Arg Gly Pro Pro Pro
465                 470                 475                 480

Arg Pro Ala Ala Asp Ser Ser Glu Ala Pro Val His Pro Ala Leu
                485                 490                 495

Ala Pro Asn Ser Ser Glu Pro Trp Val Trp Ala Gln Pro Val Thr Thr
            500                 505                 510

Gly Lys Gly Gln Asp His Ser Pro Phe Trp Gly Phe Tyr Phe Leu Leu
```

```
                        515                 520                 525
Leu Ala Val Gln Ala Met Ile Thr Val Ile Ile Val Phe Ala Met Ile
            530                 535                 540

Lys Ile Gly Gln Leu Phe Arg Lys Leu Ile Arg Glu Arg Ala Leu Gly
545                 550                 555                 560
```

(2) INFORMATION FOR SEQ ID NO:3:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:3:

```
CAGGATGCAA                                                                10
```

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:4:

```
GGGGTGTGGC                                                                10
```

(2) INFORMATION FOR SEQ ID NO:5:

(i) SEQUENCE CHARACTERISTICS:
        (A) LENGTH: 9 amino acids
        (B) TYPE: amino acid
        (D) TOPOLOGY: unknown (ii) MOLECULE TYPE: peptide (xi) SEQUENCE DESCRIPTION: SEQ ID NO:5:

```
Asn Ser Trp Arg Cys Asp Cys Gly Leu
1               5
```

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1..13
        (D) OTHER INFORMATION: /note= "K5/6 peptide residues
            1-13."

(xi) SEQUENCE DESCRIPTION: SEQ ID NO:6:

```
Lys Met Val Leu Leu Glu Gln Leu Phe Leu Asp His Asn
1               5                   10
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear

```
        (ix) FEATURE:
              (A) NAME/KEY: misc_feature
              (B) LOCATION: 1..23
              (D) OTHER INFORMATION: /standard_name= "Primer 1 (+)"
                    /note= "Oligonucleotide primer used for the PCR
                    amplification of platelet GPV."

(xi) SEQUENCE DESCRIPTION: SEQ ID NO:7:

GARCARCTGT TYCTSGAYCA YAA                                              23

(2) INFORMATION FOR SEQ ID NO:8:

(i) SEQUENCE CHARACTERISTICS:
              (A) LENGTH: 12 amino acids
              (B) TYPE: amino acid
              (D) TOPOLOGY: unknown (ii) MOLECULE TYPE: peptide (ix) FEATURE:
              (A) NAME/KEY: Peptide
              (B) LOCATION: 1..12
              (D) OTHER INFORMATION: /note= "K5/6 peptide residues
                    13-24."

(xi) SEQUENCE DESCRIPTION: SEQ ID NO:8:

Asn Ala Leu Arg Gly Ile Asp Gln Asn Met Phe Gln
1                5                  10

(2) INFORMATION FOR SEQ ID NO:9:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ix) FEATURE:
              (A) NAME/KEY: misc_feature
              (B) LOCATION: 1..32
              (D) OTHER INFORMATION: /standard_name= "Primer 2 (+)"
                    /note= "Primer used for the PCR amplification of
                    platelet GPV."

(xi) SEQUENCE DESCRIPTION: SEQ ID NO:9:

TGCGCTAAGG GGCATTGACC AAAACATGTT TC                                    32

(2) INFORMATION FOR SEQ ID NO:10:

(i) SEQUENCE CHARACTERISTICS:
              (A) LENGTH: 10 amino acids
              (B) TYPE: amino acid
              (D) TOPOLOGY: unknown (ii) MOLECULE TYPE: peptide (ix) FEATURE:
              (A) NAME/KEY: Peptide
              (B) LOCATION: 1..10
              (D) OTHER INFORMATION: /note= "K5/6 peptide residues
                    21-30."

(xi) SEQUENCE DESCRIPTION: SEQ ID NO:10:

Asn Met Phe Gln Lys Leu Val Asn Leu Gln
1                5                  10

(2) INFORMATION FOR SEQ ID NO:11:

(i) SEQUENCE CHARACTERISTICS:
              (A) LENGTH: 27 base pairs
              (B) TYPE: nucleic acid
```

-continued

```
        (C) STRANDEDNESS: single
        (D) TOPOLOGY: linear (ix) FEATURE:
        (A) NAME/KEY: misc_feature
        (B) LOCATION: 1..27
        (D) OTHER INFORMATION: /standard_name= "Primer 3(-)"
            /note= "Primer used for the PCR amplification of
            platelet GPV."

(xi) SEQUENCE DESCRIPTION: SEQ ID NO:11:

GTACAAAGTC TTTGACCAAT TGGACGT                                      27

(2) INFORMATION FOR SEQ ID NO:12:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1..11
        (D) OTHER INFORMATION: /note= "K5/6 peptide residues
            31-41."

(xi) SEQUENCE DESCRIPTION: SEQ ID NO:12:

Glu Leu Ala Leu Asn Gln Asn Gln Leu Asp Phe
1               5                   10

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: misc_feature
        (B) LOCATION: 1..21
        (D) OTHER INFORMATION: /standard_name= "Primer 4 (-)"
            /note= "Primer used for the PCR amplification of
            platelet GPV."

(xi) SEQUENCE DESCRIPTION: SEQ ID NO:13:

TTRGTYTTRG TYGASCTRAA R                                            21

(2) INFORMATION FOR SEQ ID NO:14:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (ix) FEATURE:
        (A) NAME/KEY: Peptide
        (B) LOCATION: 1..7
        (D) OTHER INFORMATION: /note= "M6 peptide residues
            1-7."

(xi) SEQUENCE DESCRIPTION: SEQ ID NO:14:

Met Ile Ser Asp Ser His Ile
1               5

(2) INFORMATION FOR SEQ ID NO:15:
```

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..20
            (D) OTHER INFORMATION: /standard_name= "Primer 5 (+)"
                /note= "Primer used for the PCR amplification of
                platelet GPV."

(xi) SEQUENCE DESCRIPTION: SEQ ID NO:15:

ATGATCTSCG AYWSCCAYAT                                                 20

(2) INFORMATION FOR SEQ ID NO:16:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..21
            (D) OTHER INFORMATION: /standard_name= "Primer 6 (+)"
                /note= "Primer used for the PCR amplification of
                platelet GPV."

(xi) SEQUENCE DESCRIPTION: SEQ ID NO:16:

GAGAGACTTC TGCTCCACTC G                                               21

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..21
            (D) OTHER INFORMATION: /standard_name= "Primer 7 (-)"
                /note= "Primer used for the PCR amplification of
                platelet GPV."

(xi) SEQUENCE DESCRIPTION: SEQ ID NO:17:

TATCAGGTCA CTGAAGGTGC C                                               21

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ix) FEATURE:
            (A) NAME/KEY: misc_feature
            (B) LOCATION: 1..18
            (D) OTHER INFORMATION: /standard_name= "Primer 8 (-)"
                /note= "Primer used for the PCR amplification of
                platelet GPV."

(xi) SEQUENCE DESCRIPTION: SEQ ID NO:18:

AAGACACACT TGCAAGCT                                                   18

(2) INFORMATION FOR SEQ ID NO:19:
```

```
     (i) SEQUENCE CHARACTERISTICS:
         (A) LENGTH: 35 base pairs
         (B) TYPE: nucleic acid
         (C) STRANDEDNESS: single
         (D) TOPOLOGY: linear (ix) FEATURE:
         (A) NAME/KEY: misc_feature
         (B) LOCATION: 1..35
         (D) OTHER INFORMATION: /standard_name= "Adaptor dT17"

(xi) SEQUENCE DESCRIPTION: SEQ ID NO:19:

GACTCGAGTC GACATCGATT TTTTTTTTTT TTTTT                                     35

(2) INFORMATION FOR SEQ ID NO:20:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ix) FEATURE:
         (A) NAME/KEY: misc_feature
         (B) LOCATION: 1..30
         (D) OTHER INFORMATION: /standard_name= "Adaptor dC12"

(xi) SEQUENCE DESCRIPTION: SEQ ID NO:20:

GACTCGAGTC GACATCGACC CCCCCCCCCC                                           30

(2) INFORMATION FOR SEQ ID NO:21:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ix) FEATURE:
         (A) NAME/KEY: misc_feature
         (B) LOCATION: 1..18
         (D) OTHER INFORMATION: /standard_name= "Adaptor"

(xi) SEQUENCE DESCRIPTION: SEQ ID NO:21:

GACTCGAGTC GACATCGA                                                        18

(2) INFORMATION FOR SEQ ID NO:22:

(i) SEQUENCE CHARACTERISTICS:
         (A) LENGTH: 24 amino acids
         (B) TYPE: amino acid
         (D) TOPOLOGY: unknown (ii) MOLECULE TYPE: peptide (ix) FEATURE:
         (A) NAME/KEY: Region
         (B) LOCATION: 1..24
         (D) OTHER INFORMATION: /note= "Tandem Leu-rich repeated
             structure for platelet GPV."

(xi) SEQUENCE DESCRIPTION: SEQ ID NO:22:

Gly Arg Gly Val Leu Gln Ser Gln Ser Phe Ser Gly Met Thr Val Leu
1               5                   10                  15

Gln Arg Leu Met Ile Ser Asp Ser
            20

(2) INFORMATION FOR SEQ ID NO:23:
```

(i) SEQUENCE CHARACTERISTICS:
    (A) LENGTH: 24 amino acids
    (B) TYPE: amino acid
    (D) TOPOLOGY: unknown (ii) MOLECULE TYPE: peptide (ix) FEATURE:
    (A) NAME/KEY: Region
    (B) LOCATION: 1..24
    (D) OTHER INFORMATION: /note= "Tandem Leu-rich repeated
        structure for platelet GPV."

(xi) SEQUENCE DESCRIPTION: SEQ ID NO:23:

His Ile Ser Ala Val Ala Pro Gly Thr Phe Ser Asp Leu Ile Lys Leu
1               5                   10                  15

Lys Thr Leu Arg Leu Ser Arg Asn
            20

(2) INFORMATION FOR SEQ ID NO:24:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:24:

Lys Ile Thr His Leu Pro Gly Ala Leu Leu Asp Lys Met Val Leu Leu
1               5                   10                  15

Glu Gln Leu Phe Leu Asp His Asn
            20

(2) INFORMATION FOR SEQ ID NO:25:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:25:

Ala Leu Arg Gly Ile Asp Gln Asn Met Phe Gln Lys Leu Val Asn Leu
1               5                   10                  15

Gln Glu Leu Ala Leu Asn Gln Asn
            20

(2) INFORMATION FOR SEQ ID NO:26:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide -continued (ix) FEATURE:
            (A) NAME/KEY: Region
            (B) LOCATION: 1..24
            (D) OTHER INFORMATION: /note= "Tandem Leu-rich repeated
                structure for platelet GPV."

(xi) SEQUENCE DESCRIPTION: SEQ ID NO:26:

Gln Leu Asp Phe Leu Pro Ala Ser Leu Phe Thr Asn Leu Glu Asn Leu
1               5                   10                  15

Lys Leu Leu Asp Leu Ser Gly Asn
            20

(2) INFORMATION FOR SEQ ID NO:27:

(i) SEQUENCE CHARACTERISTICS:
            (A) LENGTH: 24 amino acids
            (B) TYPE: amino acid
            (D) TOPOLOGY: unknown (ii) MOLECULE TYPE: peptide (ix) FEATURE:
            (A) NAME/KEY: Region
            (B) LOCATION: 1..24
            (D) OTHER INFORMATION: /note= "Tandem Leu-rich repeated
                structure for platelet GPV."

(xi) SEQUENCE DESCRIPTION: SEQ ID NO:27:

Asn Leu Thr His Leu Pro Lys Gly Leu Leu Gly Ala Gln Ala Lys Leu
1               5                   10                  15

Glu Arg Leu Leu Leu His Ser Asn
            20

(2) INFORMATION FOR SEQ ID NO:28:

(i) SEQUENCE CHARACTERISTICS:
            (A) LENGTH: 24 amino acids
            (B) TYPE: amino acid
            (D) TOPOLOGY: unknown (ii) MOLECULE TYPE: peptide (ix) FEATURE:
            (A) NAME/KEY: Region
            (B) LOCATION: 1..24
            (D) OTHER INFORMATION: /note= "Tandem Leu-rich repeated
                structure for platelet GPV."

(xi) SEQUENCE DESCRIPTION: SEQ ID NO:28:

Arg Leu Val Ser Leu Asp Ser Gly Leu Leu Asn Ser Leu Gly Ala Leu
1               5                   10                  15

Thr Glu Leu Gln Phe His Arg Asn
            20

(2) INFORMATION FOR SEQ ID NO:29:

(i) SEQUENCE CHARACTERISTICS:
            (A) LENGTH: 24 amino acids
            (B) TYPE: amino acid
            (D) TOPOLOGY: unknown (ii) MOLECULE TYPE: peptide (ix) FEATURE:
            (A) NAME/KEY: Region
            (B) LOCATION: 1..24
            (D) OTHER INFORMATION: /note= "Tandem Leu-rich repeated
                structure for platelet GPV."

(xi) SEQUENCE DESCRIPTION: SEQ ID NO:29:

```
His Ile Arg Ser Ile Ala Pro Gly Ala Phe Asp Arg Leu Pro Asn Leu
1               5                   10                  15

Ser Ser Leu Thr Leu Ser Arg Asn
            20
```

(2) INFORMATION FOR SEQ ID NO:30:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:30:

```
His Leu Ala Phe Leu Pro Ser Ala Leu Phe Leu His Ser His Asn Leu
1               5                   10                  15

Thr Leu Leu Thr Leu Phe Glu Asn
            20
```

(2) INFORMATION FOR SEQ ID NO:31:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:31:

```
Pro Leu Ala Glu Leu Pro Gly Val Leu Phe Gly Glu Met Gly Gly Leu
1               5                   10                  15

Gln Glu Leu Trp Leu Asn Arg Thr
            20
```

(2) INFORMATION FOR SEQ ID NO:32:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:32:

```
Gln Leu Arg Thr Leu Pro Ala Ala Ala Phe Arg Asn Leu Ser Arg Leu
1               5                   10                  15

Arg Tyr Leu Gly Val Thr Leu Ser
            20
```

(2) INFORMATION FOR SEQ ID NO:33:

(i) SEQUENCE CHARACTERISTICS:
        (A) LENGTH: 25 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:33:

```
Pro Arg Leu Ser Ala Leu Pro Gln Gly Ala Phe Gln Gly Leu Gly Glu
1               5                  10                  15

Leu Gln Val Leu Ala Leu His Ser Asn
            20                  25
```

(2) INFORMATION FOR SEQ ID NO:34:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:34:

```
Gly Leu Thr Ala Leu Pro Asp Gly Leu Leu Arg Gly Leu Gly Lys Leu
1               5                  10                  15

Arg Gln Val Ser Leu Arg Arg Asn
            20
```

(2) INFORMATION FOR SEQ ID NO:35:

(i) SEQUENCE CHARACTERISTICS:
        (A) LENGTH: 24 amino acids
        (B) TYPE: amino acid
        (D) TOPOLOGY: unknown (ii) MOLECULE TYPE: peptide (ix) FEATURE:
        (A) NAME/KEY: Region
        (B) LOCATION: 1..24
        (D) OTHER INFORMATION: /note= "Tandem Leu-rich repeated
            structure for platelet GPV."

(xi) SEQUENCE DESCRIPTION: SEQ ID NO:35:

```
Arg Leu Arg Ala Leu Pro Arg Ala Leu Phe Arg Asn Leu Ser Ser Leu
1               5                  10                  15

Glu Ser Val Gln Leu Asp His Asn
            20
```

(2) INFORMATION FOR SEQ ID NO:36:

(i) SEQUENCE CHARACTERISTICS:
        (A) LENGTH: 24 amino acids
        (B) TYPE: amino acid
        (D) TOPOLOGY: unknown

```
    (ii) MOLECULE TYPE: peptide (ix) FEATURE:
         (A) NAME/KEY: Region
         (B) LOCATION: 1..24
         (D) OTHER INFORMATION: /note= "Tandem Leu-rich repeated
             structure for platelet GPV."

(xi) SEQUENCE DESCRIPTION: SEQ ID NO:36:

Gln Leu Glu Thr Leu Pro Gly Asp Val Phe Gly Ala Leu Pro Arg Leu
1               5                  10                  15

Thr Glu Val Leu Leu Gly His Asn
             20

(2) INFORMATION FOR SEQ ID NO:37:

(i) SEQUENCE CHARACTERISTICS:
         (A) LENGTH: 24 amino acids
         (B) TYPE: amino acid
         (D) TOPOLOGY: unknown (ii) MOLECULE TYPE: peptide (ix) FEATURE:
         (A) NAME/KEY: Region
         (B) LOCATION: 1..24
         (D) OTHER INFORMATION: /note= "Consensus sequence for the
             tandem Leu-rich repeated structure for platelet
             GPV."

(xi) SEQUENCE DESCRIPTION: SEQ ID NO:37:

Xaa Leu Xaa Xaa Leu Pro Xaa Xaa Leu Phe Xaa Xaa Leu Xaa Xaa Leu
1               5                  10                  15

Xaa Xaa Leu Xaa Leu Xaa Xaa Asn
             20

(2) INFORMATION FOR SEQ ID NO:38:

(i) SEQUENCE CHARACTERISTICS:
         (A) LENGTH: 11 amino acids
         (B) TYPE: amino acid
         (D) TOPOLOGY: unknown (ii) MOLECULE TYPE: peptide (iii) HYPOTHETICAL: NO (ix) FEATURE:
         (A) NAME/KEY: Peptide
         (B) LOCATION: 1..11
         (D) OTHER INFORMATION: /note= "Amino acid sequence of the
             GPV thrombin cleavage site."

(ix) FEATURE:
         (A) NAME/KEY: Region
         (B) LOCATION: 1..2
         (D) OTHER INFORMATION: /note= "Amino acid residues found
             in other thrombin substrates."

(ix) FEATURE:
         (A) NAME/KEY: Region
         (B) LOCATION: 5..9
         (D) OTHER INFORMATION: /note= "Amino acid residues found
             in other thrombin substrates."

(ix) FEATURE:
         (A) NAME/KEY: Region
         (B) LOCATION: 11
         (D) OTHER INFORMATION: /note= "Amino acid residue found in
             other thrombin substrates."

(xi) SEQUENCE DESCRIPTION: SEQ ID NO:38:
```

```
Ala Glu Cys Pro Gly Pro Arg Gly Pro Pro Pro
1               5                   10
```

(2) INFORMATION FOR SEQ ID NO:39:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (iii) HYPOTHETICAL: NO (ix) FEATURE:
        (A) NAME/KEY: Peptide
        (B) LOCATION: 1..11
        (D) OTHER INFORMATION: /note= "Amino acid sequence of the
            human fibrinogen (Fg) A-alpha 1 chain thrombin
            cleavage site."

(ix) FEATURE:
        (A) NAME/KEY: Region
        (B) LOCATION: 1..2
        (D) OTHER INFORMATION: /note= "Amino acid residues
            identical to GPV."

(ix) FEATURE:
        (A) NAME/KEY: Region
        (B) LOCATION: 5
        (D) OTHER INFORMATION: /note= "Amino acid residue
            identical to GPV."

(ix) FEATURE:
        (A) NAME/KEY: Region
        (B) LOCATION: 7..9
        (D) OTHER INFORMATION: /note= "Amino acid residues
            identical to GPV."

(xi) SEQUENCE DESCRIPTION: SEQ ID NO:39:

```
Ala Glu Gly Gly Gly Val Arg Gly Pro Arg Val
1               5                   10
```

(2) INFORMATION FOR SEQ ID NO:40:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (iii) HYPOTHETICAL: NO (ix) FEATURE:
        (A) NAME/KEY: Peptide
        (B) LOCATION: 1..11
        (D) OTHER INFORMATION: /note= "Amino acid sequence of the
            human fibrinogen (Fg) A-alpha 2 chain thrombin
            cleavage site."

(ix) FEATURE:
        (A) NAME/KEY: Region
        (B) LOCATION: 5..7
        (D) OTHER INFORMATION: /note= "Amino acid residues
            identical to GPV."

(xi) SEQUENCE DESCRIPTION: SEQ ID NO:40:

```
Gly Gly Val Arg Gly Pro Arg Val Val Glu Arg
1               5                   10
```

(2) INFORMATION FOR SEQ ID NO:41:

(i) SEQUENCE CHARACTERISTICS:
            (A) LENGTH: 11 amino acids
            (B) TYPE: amino acid
            (D) TOPOLOGY: unknown (ii) MOLECULE TYPE: peptide (iii) HYPOTHETICAL: NO (ix) FEATURE:
            (A) NAME/KEY: Peptide
            (B) LOCATION: 1..11
            (D) OTHER INFORMATION: /note= "Amino acid sequence of the
                human fibrinogen (Fg) B-beta chain  thrombin
                cleavage site."

(ix) FEATURE:
            (A) NAME/KEY: Region
            (B) LOCATION: 7..8
            (D) OTHER INFORMATION: /note= "Amino acid residues
                identical to GPV."

(ix) FEATURE:
            (A) NAME/KEY: Region
            (B) LOCATION: 11
            (D) OTHER INFORMATION: /note= "Amino acid residue
                identical to GPV."

(xi) SEQUENCE DESCRIPTION: SEQ ID NO:41:

Glu Gly Phe Phe Ser Ala Arg Gly His Arg Pro
1               5                  10

(2) INFORMATION FOR SEQ ID NO:42:

(i) SEQUENCE CHARACTERISTICS:
            (A) LENGTH: 11 amino acids
            (B) TYPE: amino acid
            (D) TOPOLOGY: unknown (ii) MOLECULE TYPE: peptide (iii) HYPOTHETICAL: NO (ix) FEATURE:
            (A) NAME/KEY: Peptide
            (B) LOCATION: 1..11
            (D) OTHER INFORMATION: /note= "Amino acid sequence of the
                human plasma factor XIII (FXIII) thrombin cleavage
                site."

(ix) FEATURE:
            (A) NAME/KEY: Region
            (B) LOCATION: 6..8
            (D) OTHER INFORMATION: /note= "Amino acid residues
                identical to GPV."

(xi) SEQUENCE DESCRIPTION: SEQ ID NO:42:

Glu Leu Gln Gly Val Pro Arg Gly Val Asp Leu
1               5                  10

(2) INFORMATION FOR SEQ ID NO:43:

(i) SEQUENCE CHARACTERISTICS:
            (A) LENGTH: 11 amino acids
            (B) TYPE: amino acid
            (D) TOPOLOGY: unknown (ii) MOLECULE TYPE: peptide (iii) HYPOTHETICAL: NO (ix) FEATURE:
            (A) NAME/KEY: Peptide
            (B) LOCATION: 1..11
            (D) OTHER INFORMATION: /note= "Amino acid sequence of the

```
              human chorionic gonatropin beta-subunit (CGbeta)
              thrombin cleavage site."

(ix) FEATURE:
         (A) NAME/KEY: Region
         (B) LOCATION: 6..8
         (D) OTHER INFORMATION: /note= "Amino acid residues
              identical to GPV."

(ix) FEATURE:
         (A) NAME/KEY: Region
         (B) LOCATION: 11
         (D) OTHER INFORMATION: /note= "Amino acid residue
              identical to GPV."

(xi) SEQUENCE DESCRIPTION: SEQ ID NO:43:

Arg Leu Pro Gly Cys Pro Arg G

TABLE I

Peptide sequences and oligonucleotide primers used for the PCR amplification of platelet GPV

| | | | | | | | | | | | | | |
|---|---|---|---|---|---|---|---|---|---|---|---|---|---|
| K5/6 peptide Primer 1 (+) | K¹ | M | V | L | L 5'- | E GAG A | Q CAG A | L CTG | F TTT C | L CTG C | D GAT C | H CAT C | N¹³ AA-3' (SEQ.ID.NO. 6) (SEQ.ID.NO. 7) |
| K5/6 peptide Primer 2 (+) | N¹³ 5'-T | A GCG | L CTA | R AGG | G GGC | I ATT | D GAC | Q CAA | N AAC | M ATG | F TTT | Q²⁴ C-3' | (SEQ.ID.NO. 8) (SEQ.ID.NO. 9) |
| K5/6 peptide Primer 3 (−) | N²¹ 3'-G | M TAC | F AAA | Q GTC | K TTT | L GAC | V CAA | N TTG | L GAC | Q³⁰ GT-5' | | | (SEQ.ID.NO. 10) (SEQ.ID.NO. 11) |
| K5/6 peptide Primer 4 (−) | E³¹ | L | A | L 3'- | N TTG A | Q GTC T | N TTG A | L GAC G | Q GTC T | D CTG A | F⁴¹ AAG-5' A | | (SEQ.ID.NO. 12) (SEQ.ID.NO. 13) |
| M6 peptide Primer 5 (+) | M¹ 5'-ATG | I ATC | S TGC C | D GAT C | S TCC AG | H CAT C | I⁷ AT-3' | | | | | | (SEQ.ID.NO. 14) (SEQ.ID.NO. 15) |
| Primer 6 (+) | 5'-GAG | AGA | CTT | CTG | CTC | CAC | TCG-3' | | | | | | (SEQ.ID.NO. 16) |
| Primer 7 (+) | 5'-TAT | CAG | GTC | ACT | GAA | GGT | GCC-3' | | | | | | (SEQ.ID.NO. 17) |
| Primer 8 (−) | 5'-AAG | ACA | CAC | TTG | CAA | GCT | | | | | | | (SEQ.ID.NO. 18) |
| Adaptor-dT17 | 5'-GAC | TCG | AGT | CGA | CAT | CGA | TTT | TTT | TTT | TTT | TTT | | (SEQ.ID.NO. 19) |
| Adaptor dC12 | 5'-GAC | TCG | AGT | CGA | CAT | CGA | CCC | CCC | CCC | CCC-3' | | | (SEQ.ID.NO. 20) |
| Adaptor | 5'-GAC | TCG | AGT | CGA | CAT | CGA | CGA-3' | | | | | | (SEQ.ID.NO. 21) |

The K/6 and M6 peptide sequences were taken from ref.X and numbered accordingly. Eco RI and Sal I restriction sites were added at the 5'-end of coding (+) and non coding (−) strand primers respectively to facilitate further subcloning of the PCR products.

What is claimed is:

1. An isolated DNA constuct, comprising a polynucleotide sequence, wherein said polynucleotide sequence encodes a human glycoprotein V polypeptide having the amino acid sequence as shown in SEQ ID NO: 2.

2. The DNA construct of claim 1 wherein the polynucleotide sequence comprises the nucleotide sequence of SEQ ID NO: 1.

3. The DNA construct of claim 1 wherein the polynucleotide sequence comprises bases 2422 to 4101 of SEQ ID NO: 1.

4. The DNA constuct of any one of claims 1 to 3, wherein the polynucleotide sequence lacks introns.

5. The DNA construct of any one of claims 1 to 3, further comprising a heterologous promoter operably linked to the polynucleotide sequence.

6. The DNA construct of claim 5, wherein the promoter is capable of directing expression of the polynucleotide sequence in a eukaryote.

7. The DNA construct of claim 5, wherein the promoter is capable of directing expression of the polynucleotide sequence in a prokaryote.

8. A recombinant host cell comprising the DNA construct of claim 5.

9. The recombinant host cell of claim 8, wherein the cell is a eukaryote.

10. The recombinant host cell of claim 8, wherein the cell is a prokaryote.

11. A method for detection of cells of megakaryoblastic lineage in humans, comprising:

(a) providing a first primer, the sequence of said first primer corresponding to a portion of SEQ ID NO: 1 and having a $T_M$ of about 30°C to about 70°C;

(b) providing a second primer, the sequence of said second primer corresponding to the complement of a portion of SEQ ID NO: 1 and having a $T_M$ of about 30°C to about 70°C;

(c) isolating RNA from a cell; and (d) detecting the presence or absence of glycoprotein V RNA in said cellular RNA by the polymerase chain reaction utilizing said first and second primers, the presence of said glycoprotein V RNA indicating cells of a megakaryoblastic lineage.

12. An isolated DNA molecule comprising a polynucleotide sequence that is complementary to SEQ ID. NO. 1 and that is capable of producing a specific signal when hybridized to RNA isolated from a known megakaryoblastic cell under conditions of 0.5 M $Na_2H_2PO_4$, pH 7.2, 1 mM EDTA and 7% SDS at 65°C.

* * * * *